(12) United States Patent
Entwistle et al.

(10) Patent No.: US 8,796,287 B2
(45) Date of Patent: Aug. 5, 2014

(54) ANHYDROUS CRYSTALLINE FORMS OF N-[1-(2-ETHOXYETHYL)-5-(N-ETHYL-N-METHYLAMINO)-7-(4-METHYLPYRIDIN-2-YL-AMINO)-1H-PYRAZOLO[4,3-D]PYRIMIDINE-3-CARBONYL]METHANESULFONAMIDE

(75) Inventors: David Andrew Entwistle, Sandwich (GB); Peter Vallance Marshall, Sandwich (GB); Stefan Colin John Taylor, Sandwich (GB)

(73) Assignee: Pfizer Inc., New York, NY (US)

( * ) Notice: Subject to any disclaimer, the term of this patent is extended or adjusted under 35 U.S.C. 154(b) by 40 days.

(21) Appl. No.: 13/457,886

(22) Filed: Apr. 27, 2012

(65) Prior Publication Data

US 2012/0214827 A1   Aug. 23, 2012

Related U.S. Application Data

(62) Division of application No. 11/913,091, filed as application No. PCT/IB2006/001233 on May 3, 2006, now Pat. No. 8,227,475.

(60) Provisional application No. 60/681,711, filed on May 17, 2005, provisional application No. 60/680,445, filed on May 12, 2005.

(51) Int. Cl.
*A01N 43/90*  (2006.01)
*A61K 31/519*  (2006.01)
*C07D 487/00*  (2006.01)

(52) U.S. Cl.
USPC ..................... 514/262.1; 544/262

(58) Field of Classification Search
None
See application file for complete search history.

(56) References Cited

FOREIGN PATENT DOCUMENTS

| WO | 9306104 | 4/1993 | | |
|---|---|---|---|---|
| WO | 9307149 | 4/1993 | | |
| WO | 9312095 | 6/1993 | | |
| WO | 9400453 | 1/1994 | | |
| WO | 9405661 | 3/1994 | | |
| WO | 9519978 | 7/1995 | | |
| WO | 9849166 | 11/1998 | | |
| WO | 9924433 | 5/1999 | | |
| WO | 9954333 | 10/1999 | | |
| WO | 0024745 | 5/2000 | | |
| WO | 0118004 | 3/2001 | | |
| WO | 0127112 | 4/2001 | | |
| WO | 0127113 | 4/2001 | | |
| WO | 0200660 | 1/2002 | | |
| WO | 0210171 | 2/2002 | | |
| WO | 2004096810 | 11/2004 | | |
| WO | 2005-049617 | 6/2005 | | |
| WO | 2005049616 | 6/2005 | | |
| WO | WO2005/049616 | * | 6/2005 | ........... C07D 487/04 |
| WO | 2005097799 | 10/2005 | | |
| WO | 2006046135 | 5/2006 | | |

* cited by examiner

*Primary Examiner* — Jeffrey H Murray
(74) *Attorney, Agent, or Firm* — James T. Wasicak

(57) ABSTRACT

The invention comprises (1) anhydrous crystalline forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, (2) pharmaceutical compositions comprising at least one such form, (3) methods for the treatment of a phosphodiesterase-5-mediated condition using at least one such form, and (4) methods for preparing such forms. The compound N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide has the following structure (I).

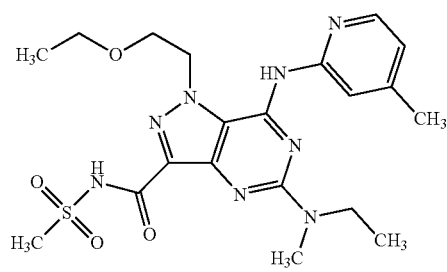

10 Claims, 15 Drawing Sheets

US 8,796,287 B2

ANHYDROUS CRYSTALLINE FORMS OF N-[1-(2-ETHOXYETHYL)-5-(N-ETHYL-N-METHYLAMINO)-7-(4-METHYLPYRIDIN-2-YL-AMINO)-1H-PYRAZOLO[4,3-D]PYRIMIDINE-3-CARBONYL]METHANESULFONAMIDE

CROSS REFERENCE TO RELATED APPLICATIONS

This application is a divisional of U.S. application Ser. No. 11/913,091, which is the National Stage of International Application No. PCT/IB2006/001233 filed May 3, 2006, which claims the benefit of priority from U.S. Provisional Application No. 60/680,445, filed May 12, 2005, and U.S. Provisional Application No. 60/681,711, filed May 17, 2005, the entire disclosures of each are herein incorporated by reference.

FIELD OF THE INVENTION

This invention relates generally to crystalline forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide. More specifically, this invention relates to (1) anhydrous crystalline forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, (2) pharmaceutical compositions comprising at least one such form, (3) methods for the treatment of a phosphodiesterase-5-mediated condition using at least one such form, and (4) methods for preparing such forms.

BACKGROUND OF THE INVENTION

The compound N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide has the following structure (1):

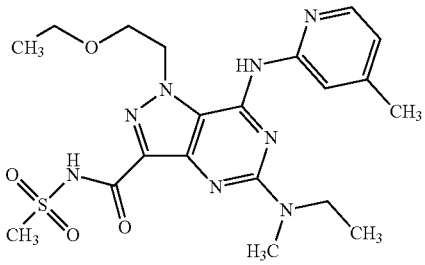

The synthesis of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide is described in Example 115 of published PCT application WO 2005/049616 (the "Compound Application"). The Compound Application further discloses that N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide is a phosphodiesterase-5 ("PDE-5") inhibitor that can be used to treat a PDE-5-mediated condition, such as hypertension.

Different solid-state forms of a pharmaceutical compound can have materially different physical properties. Such differences in physical properties can have an impact, for example, on how a pharmaceutical compound is made, processed, formulated or administered. Accordingly, the identification of new solid-state forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that provide an advantage relative to other solid-state forms in making, processing, formulating or administering the compound are desirable. As discussed below, three new anhydrous crystalline forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide have been identified.

SUMMARY OF THE INVENTION

In one embodiment, the present invention is directed to anhydrous crystalline forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

In another embodiment, the invention is directed to the Form A anhydrous crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide ("Form A").

In another embodiment, the invention is directed to the Form B anhydrous crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide ("Form B").

In another embodiment, the invention is directed to the Form C anhydrous crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide ("Form C").

In another embodiment, the invention is directed to a composition comprising at least two forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide selected from the group consisting of Form A, Form B, and Form C.

In another embodiment, the invention is directed to a pharmaceutical composition comprising at least one form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide selected from the group consisting of Form A, Form B, and Form C and a pharmaceutically acceptable carrier.

In another embodiment, the invention is directed to methods for the treatment of a PDE-5-mediated condition comprising administering to a subject a therapeutically-effective amount at least one form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide selected from the group consisting of Form A, Form B, and Form C.

In another embodiment, the invention is directed to methods for the preparation of Form A, Form B, and Form C.

Additional embodiments of the invention are discussed throughout the specification of this application.

DETAILED DESCRIPTION OF THE PREFERRED EMBODIMENTS

Figure 1:
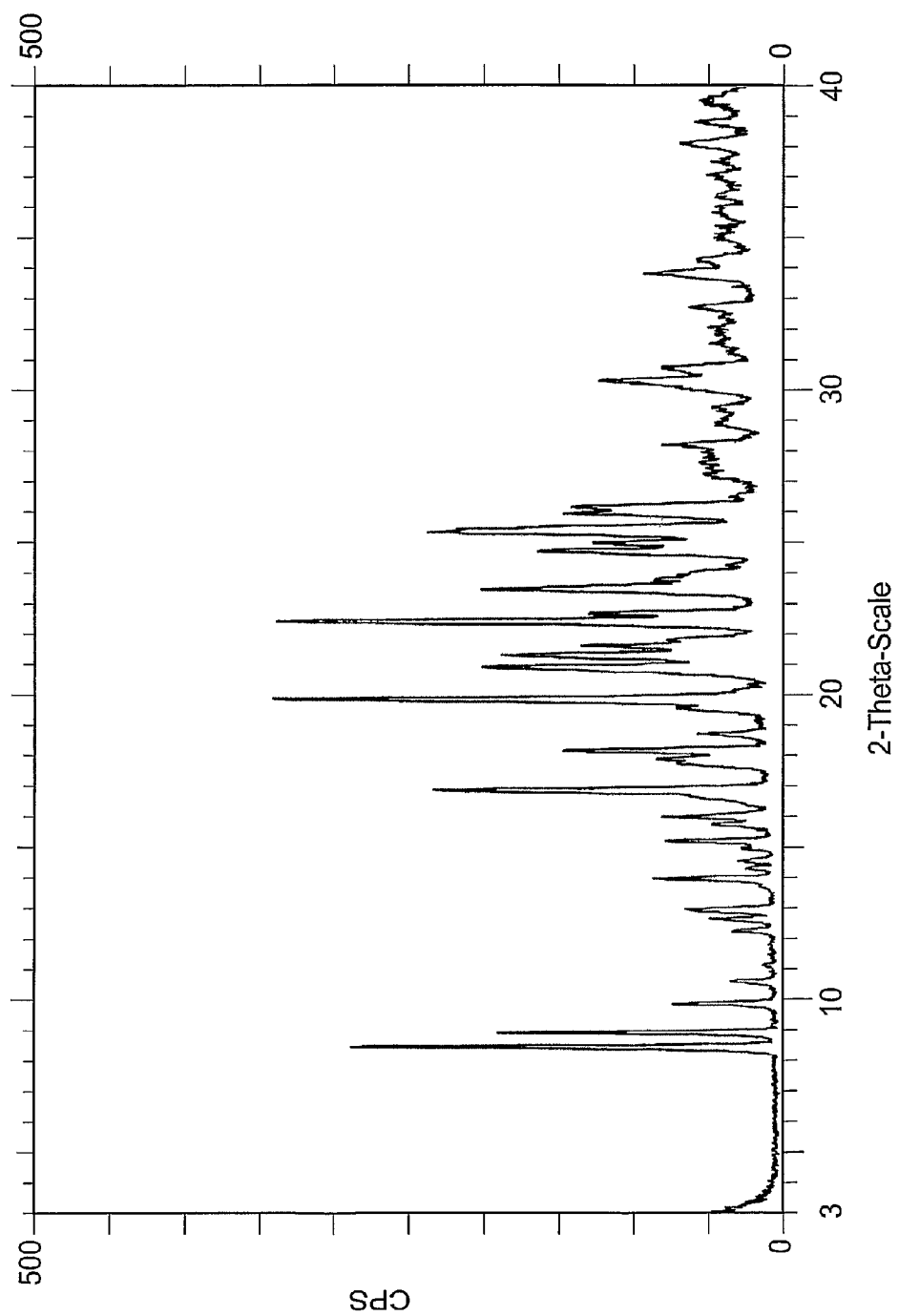
FIG. 1 shows an illustrative X-ray powder diffraction pattern for Form A.

The solid-state form of a compound can materially affect the physical properties of the compound including: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; or (6) filtration properties. Selection and control of the solid-state form is particularly important for compounds that are pharmacological agents. Careful selection and control of the solid-state form can reduce synthesis, processing, formulation or administration problems associated with the compound.

Three new anhydrous crystalline forms (Form A, Form B and Form C) of the compound N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide have been identified. As explained in greater detail below, Form A, Form B, and Form C each have distinct physical properties relative to each other.

As used in this application, the nomenclature "N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide" (as well as the corresponding "structure 1") is intended to embrace all tautomeric isomers of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide. For example, two tautomeric isomers of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide are shown below as Tautomer (1) and Tautomer (2) (exemplified by the resonance structures below):

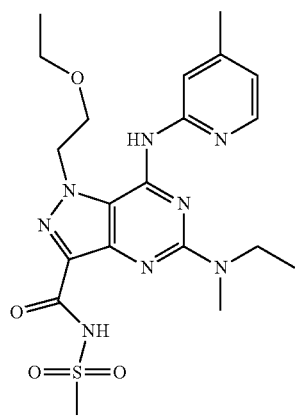
Tautomer (1)

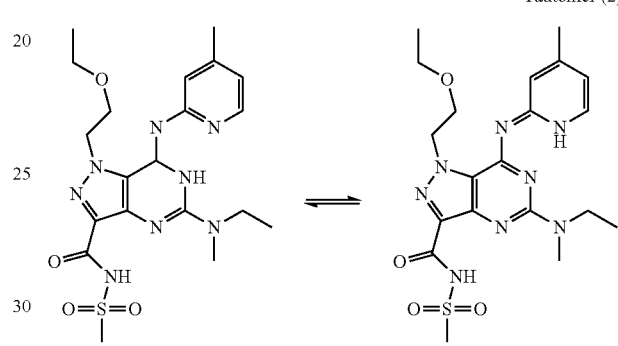
Tautomer (2)

Without being held to a particular theory, it is hypothesized that Form A crystallizes as Tautomer (1) above, and that Form B and Form C each crystallize as Tautomer (2) above.

A. ABBREVIATIONS AND DEFINITIONS

As used in reference to $^1$H NMR, the symbol "δ" refers to a $^1$H NMR chemical shift.

As used in reference to $^1$H NMR, the abbreviation "br" refers to a broad $^1$H NMR signal.

As used in reference to $^1$H NMR, the abbreviation "d" refers to a doublet $^1$H NMR peak.

The abbreviation "m/z" refers to a Mass spectrum peak.

As used in reference to $^1$H NMR, the abbreviation "m" refers to a multiplet $^1$H NMR peak.

As used in reference to $^1$H NMR, the abbreviation "q" refers to a quartet $^1$H NMR peak.

As used in reference to $^1$H NMR, the abbreviation "s" refers to a singlet $^1$H NMR peak.

As used in reference to $^1$H NMR, the abbreviation "t" refers to a triplet $^1$H NMR peak.

The term "DSC" refers to differential scanning calorimetry.

The term "HPLC" refers to high pressure liquid chromatography.

The term "PXRD" refers to X-ray powder diffraction

The terms "PDE-5-mediated condition" and "phosphodiesterase-5-mediated condition" refer to any condition mediated by PDE-5, whether through direct regulation by PDE-5, or through indirect regulation by PDE-5 as a component of a signaling pathway.

The term "composition" refers to an article of manufacture which results from the mixing or combining of more than one element or ingredient.

The term "crystalline form" as applied to N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide refers to a solid-state form wherein the N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide molecules are arranged to form a distinguishable crystal lattice (i) comprising distinguishable unit cells, and (ii) yielding diffraction peaks when subjected to X-ray radiation.

The term "crystallization" as used throughout this application can refer to crystallization and/or recrystallization depending upon the applicable circumstances relating to the preparation of the N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide starting material.

The term "purity" refers to the chemical purity of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide according to conventional HPLC assay.

The term "phase purity" refers to the solid-state purity of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide with regard to a particular solid-state form of the N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide as determined by the analytical methods described herein.

The term "pharmaceutically acceptable carrier" refers to a carrier that is compatible with the other ingredients of the composition and is not deleterious to the subject. Such carriers may be pharmaceutically acceptable material, composition or vehicle, such as a liquid or solid filler, diluent, excipient, solvent or encapsulating material, involved in carrying or transporting a chemical agent. The preferred composition depends on the method of administration.

The terms "prevent," "prevention" or "preventing" refer to either preventing the onset of a preclinically evident condition altogether or preventing the onset of a preclinical evident stage of a condition in a subject. Prevention includes, but is not limited to, prophylactic treatment of a subject at risk of developing a condition.

The term "relative intensity" refers to the ratio of the intensity of an individual diffraction peak (or spectral line as the case may be) to the intensity of the strongest diffraction peak in the same diffraction pattern. In other words, the intensity of the strongest peak is set to 100 and all other intensities are scaled accordingly.

The term "therapeutically effective amount" refers to that amount of drug or pharmaceutical agent that will elicit the biological or medical response of a tissue, system or animal that is being sought by a researcher or clinician.

The term "treatment" (and corresponding terms "treat" and "treating") refers to palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

B. CHARACTERIZATION OF CRYSTALLINE FORMS

The crystalline state of a compound can be described by several crystallographic parameters, including single crystal structure, X-ray powder diffraction pattern, melting temperature, infrared absorption spectroscopy pattern, and Raman spectroscopy pattern.

1. Single Crystal X-Ray Analysis

The crystal structure of Form A was determined by single crystal X-ray diffraction analysis. The single crystal X-ray diffraction data used in the analysis were collected at room temperature using a Bruker SMART APEX Single Crystal X-Ray diffractometer and Mo Kα radiation. Intensities were integrated (SMART v5.622 (control) and SAINT v6.02 (integration) software, Bruker AXS Inc., Madison, Wis. 1994) from several series of exposures where each exposure covered 0.3° in ω, with an exposure time of 30 seconds and the total data set was more than a hemisphere. Data were corrected for absorption using the multiscans method (SADABS, Program for scaling and correction of area detector data, G. M. Sheldrick, University of Göttingen, 1997 (based on the method of R. H. Blessing, Acta Cryst. 1995, A51, 33-38)). The crystal structure was then solved by direct methods using SHELXS-97 (Program for crystal structure refinement. G. M. Sheldrick, University of Göttingen, Germany, 1997, release 97-2), in Space Group P2$_1$/c and refined by the method of least-squares using SHELXL-97. Selected crystal structure data are summarized in Table 1A.

The crystal structure of Form C was also determined by single crystal X-ray diffraction analysis in the same manner as described above for Form A except that an exposure time of 120 seconds was used. The crystal structure was solved by direct methods using SHELXS-97, in Space Group P-1, and refined by the method of least-squares using SHELXL-97. Selected crystal structure data for Form C are summarized in Table 1B.

TABLE 1A

Form A Crystal Structure Data

| Parameter | Value |
| --- | --- |
| Crystal System | Monoclinic |
| Space Group | P2$_1$/c |
| a | 12.9809(11) Å |
| b | 18.1064(15) Å |
| c | 21.0685(17) Å |
| alpha | 90° |
| beta | 98.832(2)° |
| gamma | 90° |
| Wavelength | 0.71073 Å |
| Volume | 4893.2(7) Å$^3$ |
| Z | 8 |
| Density (calculated) | 1.294 Mg/m$^3$ |

TABLE 1B

Form C Crystal Structure Data

| Parameter | Value |
| --- | --- |
| Crystal System | Triclinic |
| Space Group | P-1 |
| a | 6.935(4) Å |
| b | 12.734(7) Å |
| c | 13.350(7) Å |
| alpha | 100.252(9)° |
| beta | 91.272(11)° |
| gamma | 95.544(10)° |
| Wavelength | 0.71073 Å |
| Volume | 1153.8(11) Å$^3$ |
| Z | 2 |
| Density (calculated) | 1.372 Mg/m$^3$ |

As previously noted, it is hypothesized that Form A crystallizes as Tautomer (1) and Form C crystallizes as Tautomer (2). Single crystal X-ray analysis supports this hypothesis.

2. X-Ray Powder Diffraction

The crystal structures of Form A, Form B and Form C were analyzed using X-ray powder diffraction ("PXRD"). The X-ray diffraction data were collected at room temperature using a Bruker AXS D4 powder X-ray diffractometer (Cu Kα radiation) fitted with an automatic sample changer, a theta-theta goniometer, automatic beam divergence slits, a secondary monochromator and a scintillation counter. Samples were prepared for analysis by packing the powder into a 12 mm diameter, 0.25 mm deep cavity that had been cut into a silicon wafer specimen mount. The sample was rotated while being irradiated with copper K-alpha$_1$ X-rays (wavelength=1.5406 Ångstroms) with the X-ray tube operated at 40 kV/40 mA. The analyses were performed with the goniometer running in continuous mode set for a 5 second count per 0.02° step over a two theta range of 2° to 55°. The peaks obtained for Form A were aligned against those from the calculated pattern from the single crystal structure. For Form B and Form C, the peaks obtained were aligned against a silicon reference standard.

For Form A, 2-theta angles, d spacings, and relative intensities were calculated from the single crystal structure using the "Reflex Powder Diffraction" module of Accelrys Materials Studio™ [version 2.2]. Pertinent simulation parameters were in each case: Wavelength=1.540562 Å (Cu K-alpha$_1$), Polarisation Factor=0.5; and Pseudo-Voigt Profile (U=0.01, V=−0.001, W=0.002).

As will be appreciated by the skilled crystallographer, the relative intensities of the various peaks reported in the Tables and Figures below may vary due to a number of factors such as orientation effects of crystals in the X-ray beam or the purity of the material being analyzed or the degree of crystallinity of the sample. The peak positions may also shift for variations in sample height but the peak positions will remain substantially as defined in Tables 2A, 2C, and 2D for Form A, Form B and Form C, respectively. The skilled crystallographer also will appreciate that measurements using a different wavelength will result in different shifts according to the Bragg equation −nλ=2d sin θ, Such further PXRD patterns generated by use of alternative wavelengths are considered to be alternative representations of the PXRD patterns of the crystalline materials of the present invention and as such are within the scope of the present invention.

Figure 3:
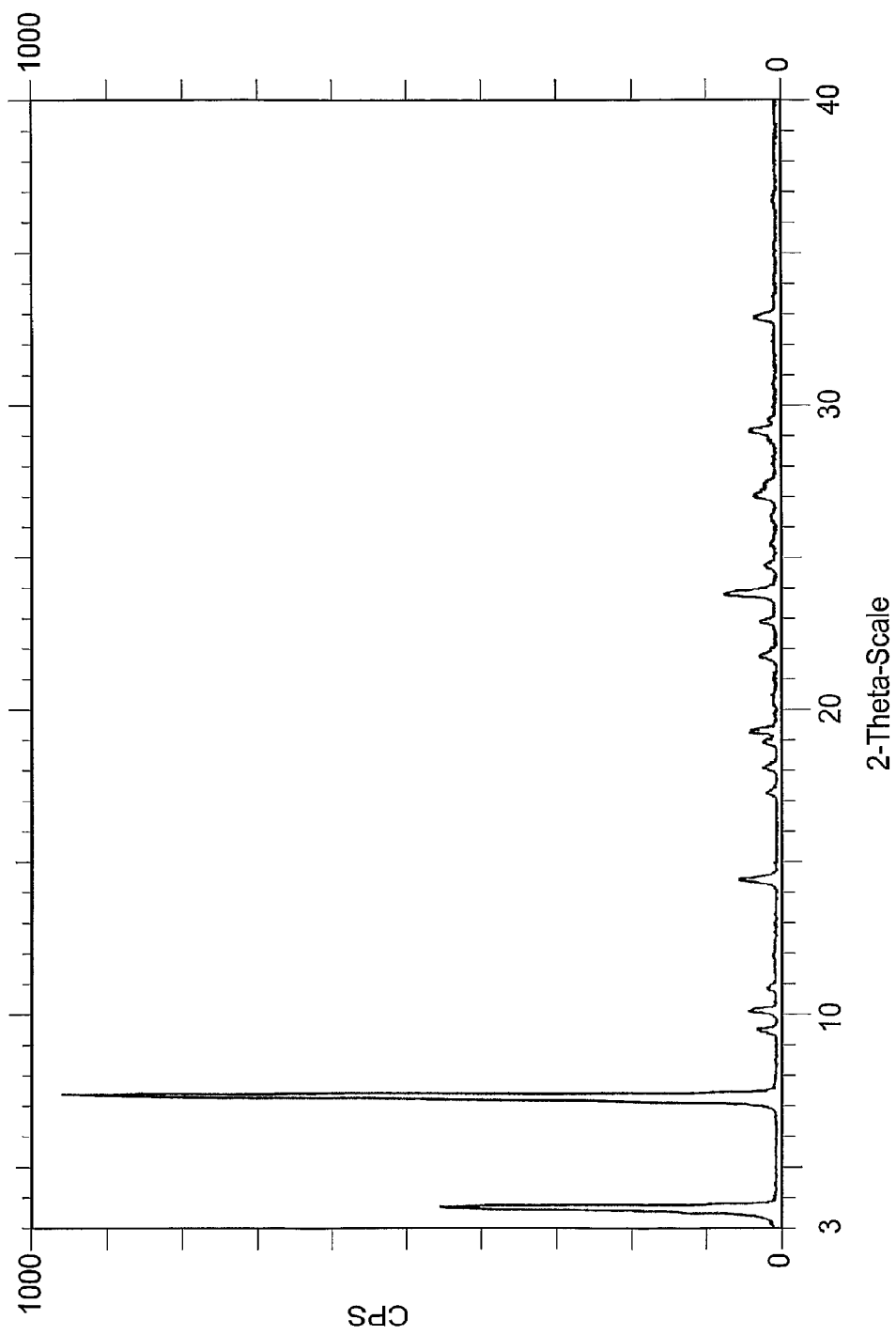
FIG. 3 shows an illustrative X-ray powder diffraction pattern for Form B.
Figure 4:
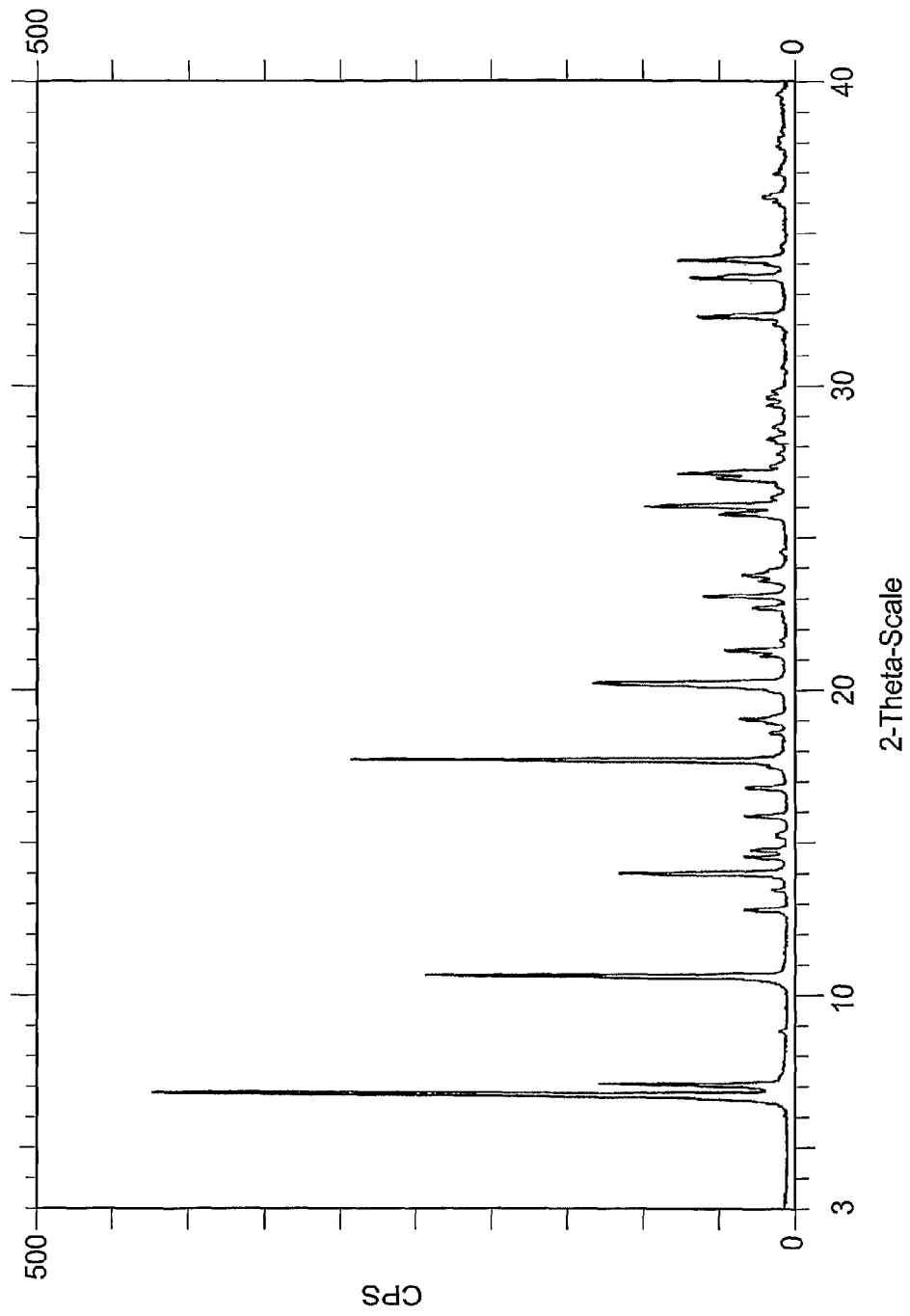
FIG. 4 shows an illustrative X-ray powder diffraction pattern for Form C.

Illustrative PXRD patterns for Form A, Form B and Form C are shown in FIGS. 1, 3 and 4, respectively. Tables 2A, 2C and 2D list the corresponding main diffraction peaks in terms of 2θ values and intensities for Form A, Form B and Form C, respectively. Table 2A lists the Form A peaks having a relative intensity greater than 25%. Table 2C lists the Form B peaks having a relative intensity greater than 2%. Table 2D lists the Form C peaks having a relative intensity greater than 10%.

Figure 2:
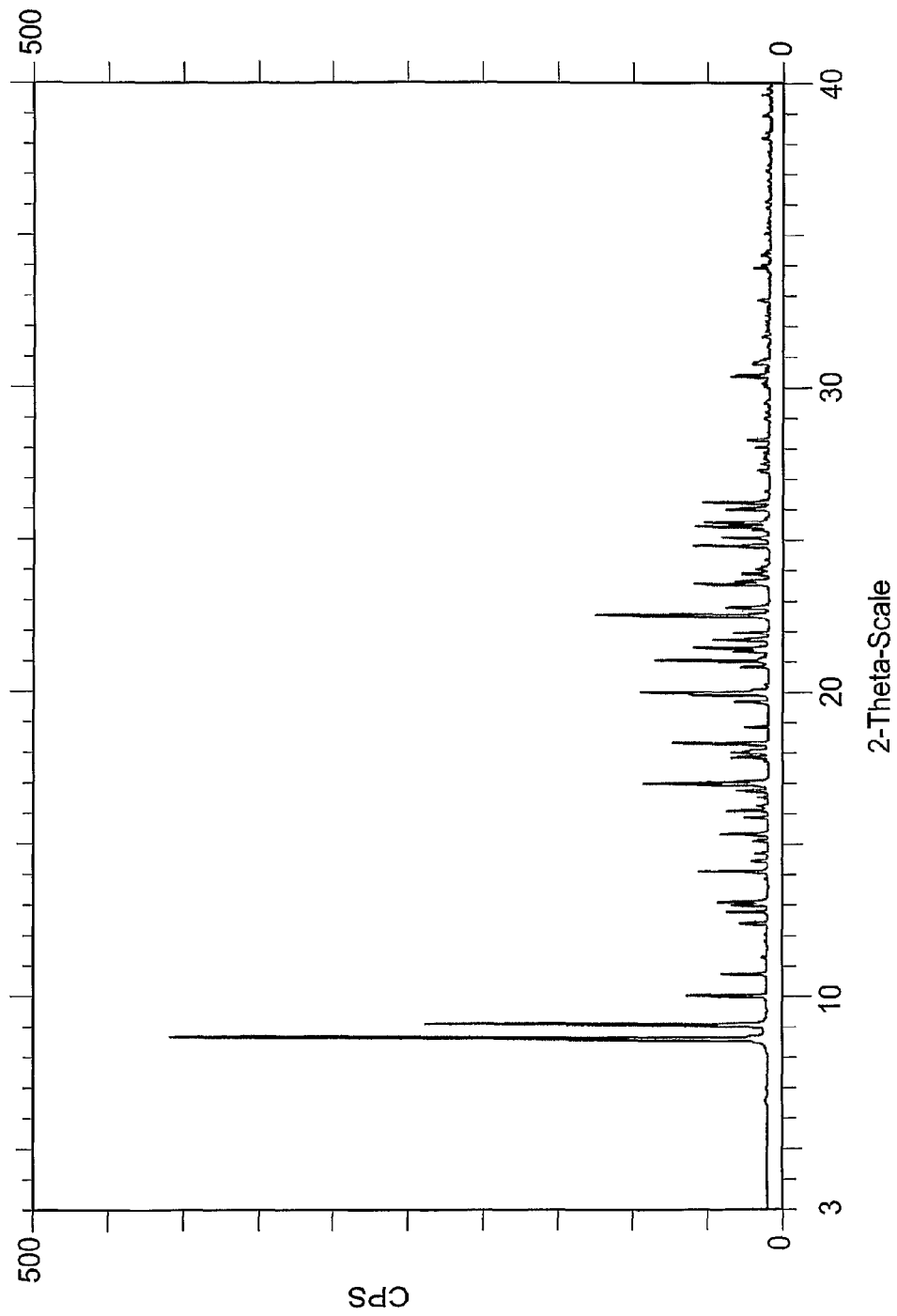
FIG. 2 shows a calculated X-ray powder diffraction pattern for Form A.

In addition, a calculated PXRD pattern for Form A is shown in FIG. 2. Table 2B lists the corresponding calculated main diffraction peaks in terms of 2θ values and intensities for Form A. Table 2B lists the calculated Form A peaks having a relative intensity greater than 10%.

TABLE 2A

Form A PXRD Data

| Angle 2-Theta (degrees) | Relative Intensity (%) |
|---|---|
| 8.5 | 84.3 |
| 9.0 | 55.8 |
| 14.0 | 25.3 |
| 16.9 | 68.5 |
| 18.2 | 42.9 |
| 19.9 | 100.0 |
| 21.0 | 58.9 |
| 21.4 | 55.0 |
| 21.7 | 39.4 |
| 22.5 | 99.1 |
| 22.7 | 37.9 |
| 23.5 | 59.2 |
| 23.9 | 25.2 |
| 24.8 | 47.7 |
| 25.0 | 37.0 |
| 25.4 | 65.8 |
| 26.0 | 42.9 |
| 26.2 | 41.3 |
| 30.3 | 36.0 |
| 33.9 | 27.2 |

TABLE 2B

Form A Calculated PXRD Data

| Angle 2-Theta (degrees) | Relative Intensity (%) |
|---|---|
| 8.5 | 100.0 |
| 9.0 | 57.9 |
| 9.9 | 14.5 |
| 13.0 | 10.2 |
| 14.1 | 12.6 |
| 16.9 | 22.2 |
| 17.0 | 12.0 |
| 18.3 | 17.3 |
| 19.9 | 15.1 |
| 20.0 | 22.7 |
| 21.0 | 20.3 |
| 21.4 | 14.0 |
| 21.7 | 10.7 |
| 22.5 | 30.2 |
| 23.6 | 13.9 |
| 24.8 | 14.2 |
| 25.5 | 13.7 |
| 26.3 | 12.3 |

TABLE 2C

Form B PXRD Data

| Angle 2-Theta (degrees) | Relative Intensity (%) |
|---|---|
| 3.6 | 47.3 |
| 7.2 | 100.0 |
| 9.4 | 2.9 |
| 10.1 | 4.1 |
| 14.4 | 5.8 |
| 18.1 | 2.2 |
| 18.9 | 2.2 |
| 19.3 | 3.8 |
| 19.4 | 3.2 |
| 21.8 | 2.7 |
| 22.9 | 2.5 |
| 23.8 | 7.6 |
| 27.0 | 3.6 |

TABLE 2C-continued

Form B PXRD Data

| Angle<br>2-Theta<br>(degrees) | Relative<br>Intensity<br>(%) |
|---|---|
| 29.1 | 4.1 |
| 32.9 | 3.5 |

TABLE 2D

Form C PXRD Data

| Angle<br>2-Theta<br>(Degrees) | Relative<br>Intensity % |
|---|---|
| 6.7 | 100.0 |
| 7.1 | 29.9 |
| 10.6 | 57.4 |
| 12.8 | 7.3 |
| 14.0 | 27.1 |
| 14.5 | 7.4 |
| 14.8 | 6.3 |
| 15.9 | 7.3 |
| 16.8 | 7.1 |
| 17.7 | 69.3 |
| 19.1 | 8.2 |
| 20.2 | 31.2 |
| 21.4 | 10.5 |
| 23.1 | 13.8 |
| 23.8 | 7.7 |
| 25.8 | 11.2 |
| 26.1 | 23.1 |
| 27.0 | 11.9 |
| 27.2 | 17.7 |
| 32.3 | 14.9 |
| 33.6 | 16.0 |
| 34.2 | 16.7 |

Form A PXRD

Form A has a PXRD pattern that comprises at least one diffraction peak selected from the group consisting of 8.5±0.1; 9.0±0.1; 16.9±0.1; 20.0±0.1; and 22.5±0.1 degrees two theta. In one embodiment, Form A has a PXRD pattern that comprises a diffraction peak at 8.5±0.1 degrees two theta. In another embodiment, Form A has a PXRD pattern that comprises a diffraction peak at 8.5±0.1 degrees two theta, and further comprises at least one additional diffraction peak selected from the group consisting of 9.0±0.1; 16.9±0.1; 20.0±0.1; and 22.5±0.1 degrees two theta. In another embodiment, Form A has a PXRD pattern that comprises diffraction peaks at 8.5±0.1; 9.0±0.1; and 16.9±0.1 degrees two theta. In another embodiment, Form A has a PXRD pattern that comprises diffraction peaks at 8.5±0.1; 9.0±0.1; 16.9±0.1; 20.0±0.1; and 22.5±0.1 degrees two theta. In the above embodiments, the diffraction peaks identified at 8.5±0.1; 9.0±0.1; 16.9±0.1; 20.0±0.1; and 22.5±0.1 degrees two theta typically have a relative intensity of at least about 10%.

In another embodiment, Form A has a PXRD pattern that (a) comprises at least one diffraction peak selected from the group consisting of 8.5±0.1; 9.0±0.1; 16.9±0.1; 20.0±0.1; and 22.5±0.1 degrees two theta, and (b) does not comprise at least one diffraction peak selected from the group consisting of 3.6±0.1 and 7.2±0.1 degrees two theta.

Form B PXRD

Form B has a PXRD pattern that comprises at least one diffraction peak selected from the group consisting of 3.6±0.1; 7.2±0.1, 10.1±0.1, 14.4±0.1 and 23.8±0.1 degrees two theta. In one embodiment, Form B has a PXRD pattern that comprises a diffraction peak at 3.6±0.1 degrees two theta. In another embodiment, Form B has a PXRD pattern that comprises a diffraction peak at 3.6±0.1 degrees two theta, and further comprises at least one additional diffraction peak selected from the group consisting of 7.2±0.1, 10.1±0.1, 14.4±0.1 and 23.8±0.1 degrees two theta. In another embodiment, Form B has a PXRD pattern that comprises diffraction peaks at 3.6±0.1 and 7.2±0.1 degrees two theta. In another embodiment, Form B has a PXRD pattern that comprises diffraction peaks at 3.6±0.1; 7.2±0.1; and 23.8±0.1 degrees two theta. In another embodiment, Form B has a PXRD pattern that comprises diffraction peaks at 3.6±0.1; 7.2±0.1; 10.1±0.1; 14.4±0.1; and 23.8±0.1 degrees two theta. In the above embodiments, the diffraction peaks identified at 3.6±0.1 and 7.2±0.1 degrees two theta typically have a relative intensity of at least about 10%.

In another embodiment, Form B has a PXRD pattern that (a) comprises at least one diffraction peak selected from the group consisting of 3.6±0.1; 7.2±0.1, 10.1±0.1, 14.4±0.1; and 23.8±0.1 degrees two theta, and (b) does not comprise at least one diffraction peak selected from the group consisting of 8.5±0.1; 6.7±0.1; and 22.5±0.1 degrees two theta.

Form C PXRD

Form C has a PXRD pattern that comprises at least one diffraction peak selected from the group consisting of and 6.7±01, 10.6±0.1; 14.0±0.1; 17.7±0.1; and 20.2±0.1 degrees two theta. In one embodiment, Form C has a PXRD pattern that comprises a diffraction peak at 6.7±0.1 degrees two theta. In one embodiment, Form C has a PXRD pattern that comprises a diffraction peak at 10.6±0.1 degrees two theta. In one embodiment, Form C has a PXRD pattern that comprises a diffraction peak at 14.0±0.1 degrees two theta. In one embodiment, Form C has a PXRD pattern that comprises a diffraction peak at 17.7±0.1 degrees two theta. In one embodiment, Form C has a PXRD pattern that comprises a diffraction peak at 20.2±0.1 degrees two theta. In another embodiment, Form C has a PXRD pattern that comprises a diffraction peak at 6.7±0.1 degrees two theta, and further comprises at least one additional diffraction peak selected from the group consisting 10.6±0.1; 14.0±0.1; 17.7±0.1; and 20.21±0.1 degrees two theta. In another embodiment, Form C has a PXRD pattern that comprises diffraction peaks at 6.7±0.1 and 20.2±0.1 degrees two theta. In another embodiment, Form C has a PXRD pattern that comprises diffraction peaks at 6.7±0.1; 17.7±0.1; and 20.2±0.1 degrees two theta. In another embodiment, Form C has a PXRD pattern that comprises diffraction peaks at 6.7±0.1; 17.7±0.1; 10.6±0.1; and 20.2±0.1 degrees two theta. In another embodiment, Form C has a PXRD pattern that comprises diffraction peaks at 6.7±0.1; 10.6±0.1; 14.0±0.1; 17.7±0.1; and 20.2±01 degrees two theta. In the above embodiments, the diffraction peaks identified at 6.7±0.1; 10.6±0.1; 14.0±0.1; 17.7±0.1; and 20.2±0.1 degrees two theta preferably have a relative intensity of at least about 10%.

In another embodiment, Form C has a PXRD pattern that (a) comprises at least one diffraction peak selected from the group consisting of 6.7±0.1; 10.6±0.1; 14.0±0.1; 17.7±0.1; and 20.2±0.1 degrees two theta, and (b) does not comprise at least one diffraction peak selected from the group consisting of 3.6±0.1 and 9.0±0.1 degrees two theta.

3. Differential Scanning Calorimetry

Form A, Form B and Form C were each analyzed using differential scanning calorimetry (DSC). A TA Instruments Q1000 differential scanning calorimeter was used to perform each analysis. Each sample was heated from 25 to 300° C. at 20° C. per minute in an aluminium pan with the lid laid on top, with a nitrogen purge gas. The temperature of the melting endothermic peak was reported as the melting point. The data from DSC analyses are dependent on several factors, including the rate of heating, the purity of the sample, crystal size, and sample size. Therefore, the following melting points are representative of the samples as prepared below.

Form A DSC

Figure 5:
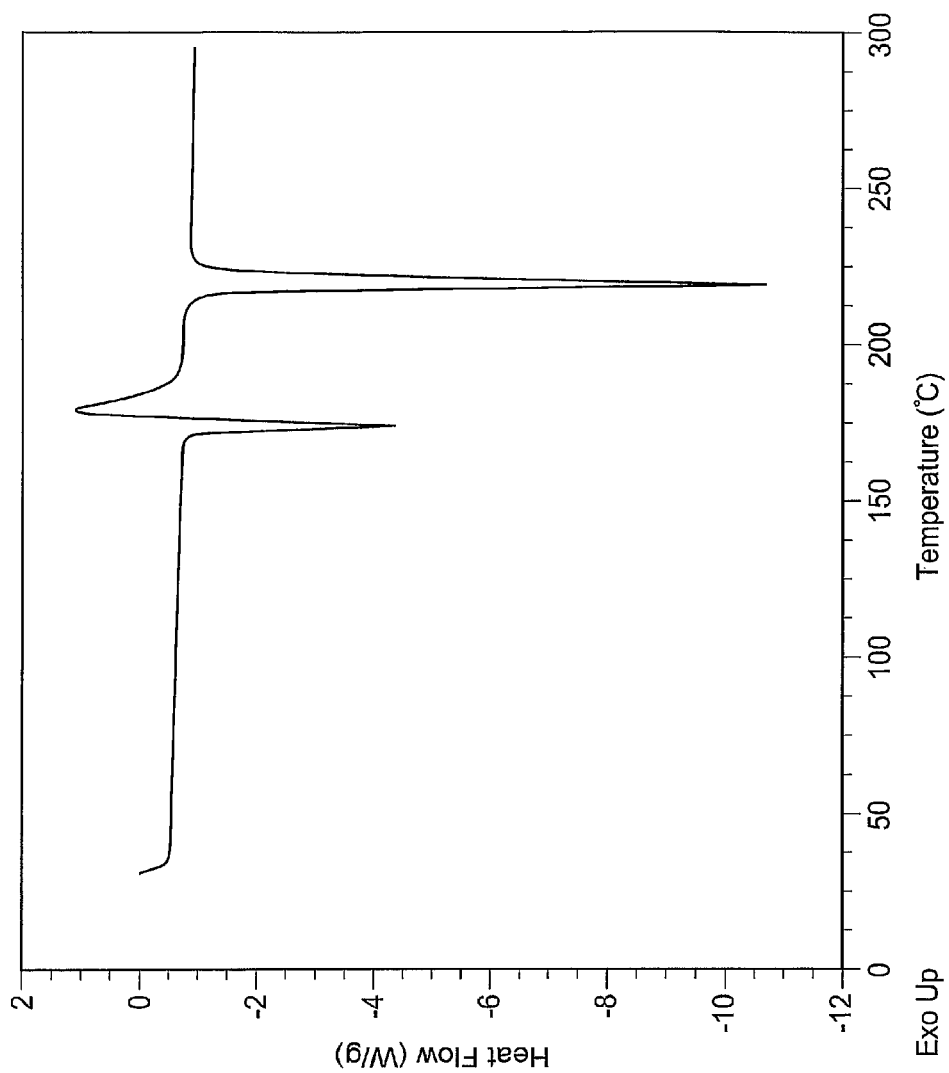
FIG. 5 shows an illustrative DSC thermogram for Form A.

A 3.171 mg sample of Form A was analyzed by DSC as described above. The DSC thermogram obtained for the sample of Form A is shown in FIG. 5. Form A shows a first endothermic peak at 174° C.±3° C., followed by an exothermic recrystallization event at 179° C.±3° C., and a second endothermic peak at 219° C.±3° C. The peak at 174° C.±3° C. corresponds to the melting of Form A. The exothermic recrystallisation event at 179° C.±3° C. corresponds to the recrystallization of the melted compound as Form B. The peak at 219° C.±3° C. corresponds to the melting of Form B.

Form B DSC

Figure 6:
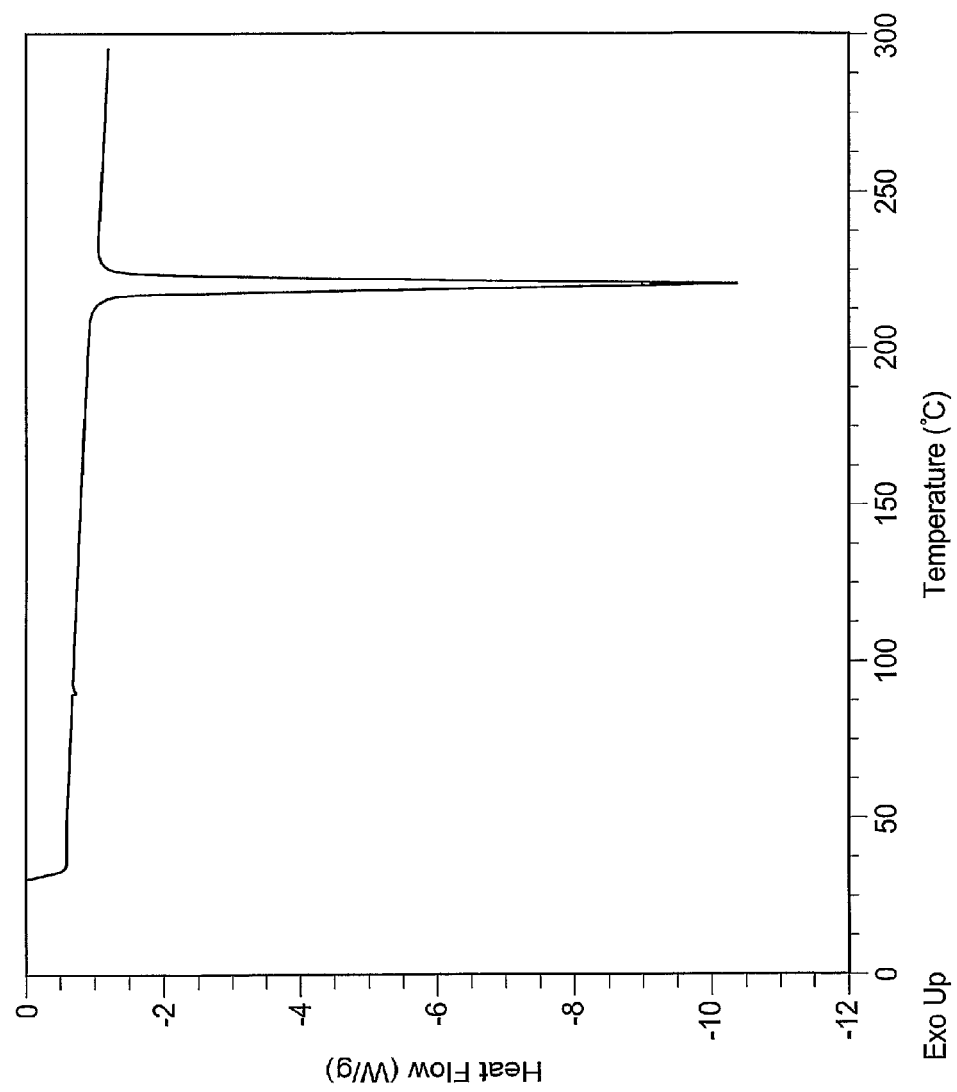
FIG. 6 shows an illustrative DSC thermogram for Form B.

A 1.603 mg sample of Form B was analyzed by DSC as described above. The DSC thermogram for obtained for the sample of Form B is shown in FIG. 6. Form B shows an endothermic peak at 218° C.±3° C. that corresponds to the melting of Form B.

Form C DSC

Figure 7:
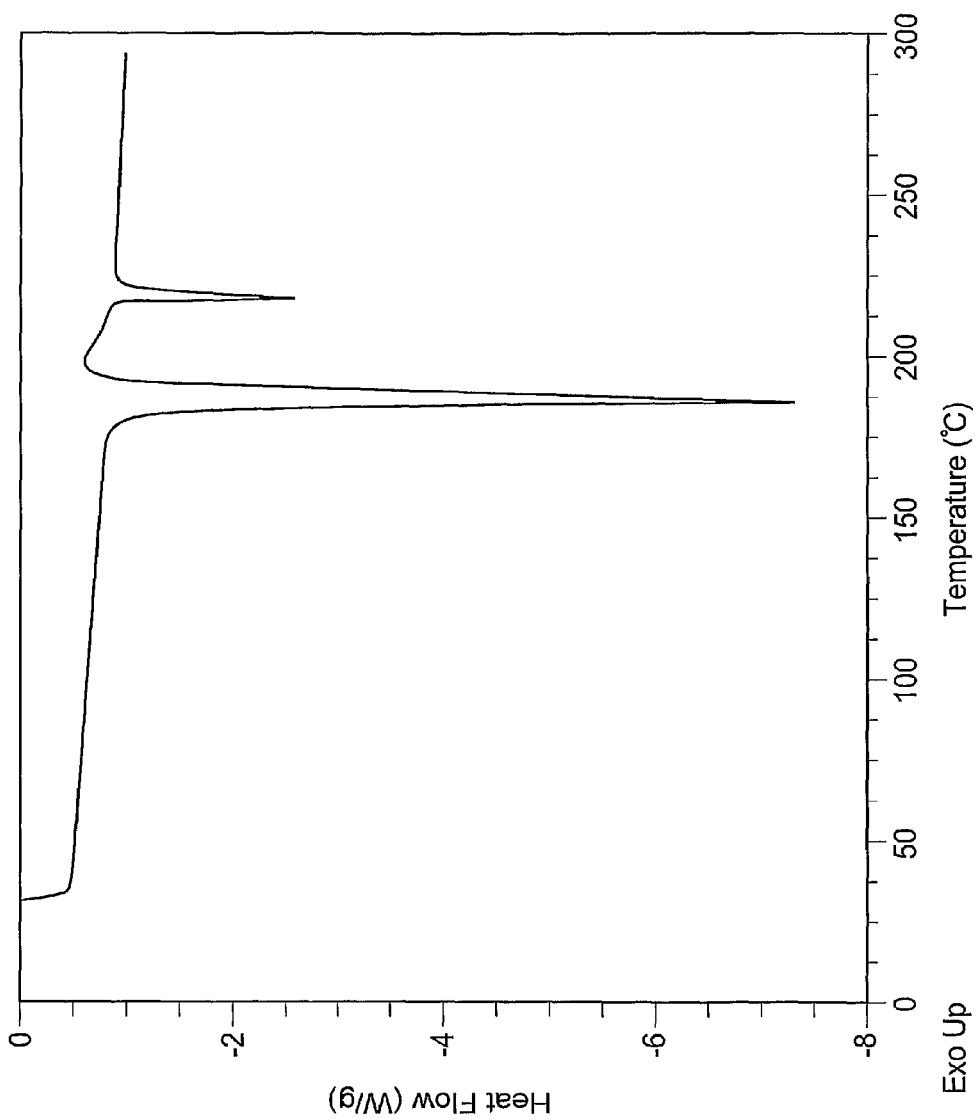
FIG. 7 shows an illustrative DSC thermogram for Form C.

A 4.405 mg sample of Form C was analyzed by DSC as described above. The DSC thermogram for obtained for the sample of Form C is shown in FIG. 7. Form C shows a first endothermic peak at 188° C.±3° C., followed by an exothermic recrystallization event at 199° C.±3° C., and a second endotherm at 219° C.±3° C. The peak at 188° C.±3° C. corresponds to the melting of Form C. The exothermic recrystallisation event at 199° C.±3° C. corresponds to the recrystallization of the melted compound as Form B. The peak at 219° C.±3° C. corresponds to the melting of Form B.

4. Fourier-Transform Infrared Spectroscopy

The crystal structures of Form A, Form B and Form C were analyzed using Fourier-Transform infrared ("FT-IR") spectroscopy. FT-IR spectra for samples of Form A, Form B and Form C were obtained using a ThermoNicolet Avatar 360 spectrometer with a Smart Golden Gate single reflection ATR accessory (diamond top-plate and zinc-selenide lenses). The measurements were collected using 2 cm-1 resolution, 128 scans, and Happ Genzel apodization. Because the FT-IR spectra were recorded using single reflection ATR, no sample preparation was required. Using ATR FT-IR, however, will cause the relative intensities of infrared bands to differ from those typically seen in a KBr disc FT-IR spectrum. Due to the nature of ATR FT-IR, band intensities generally increase when going from the higher wavenumber region to the lower wavenumber region. Experimental error, unless otherwise noted, was ±2 cm-1.

Figure 8:
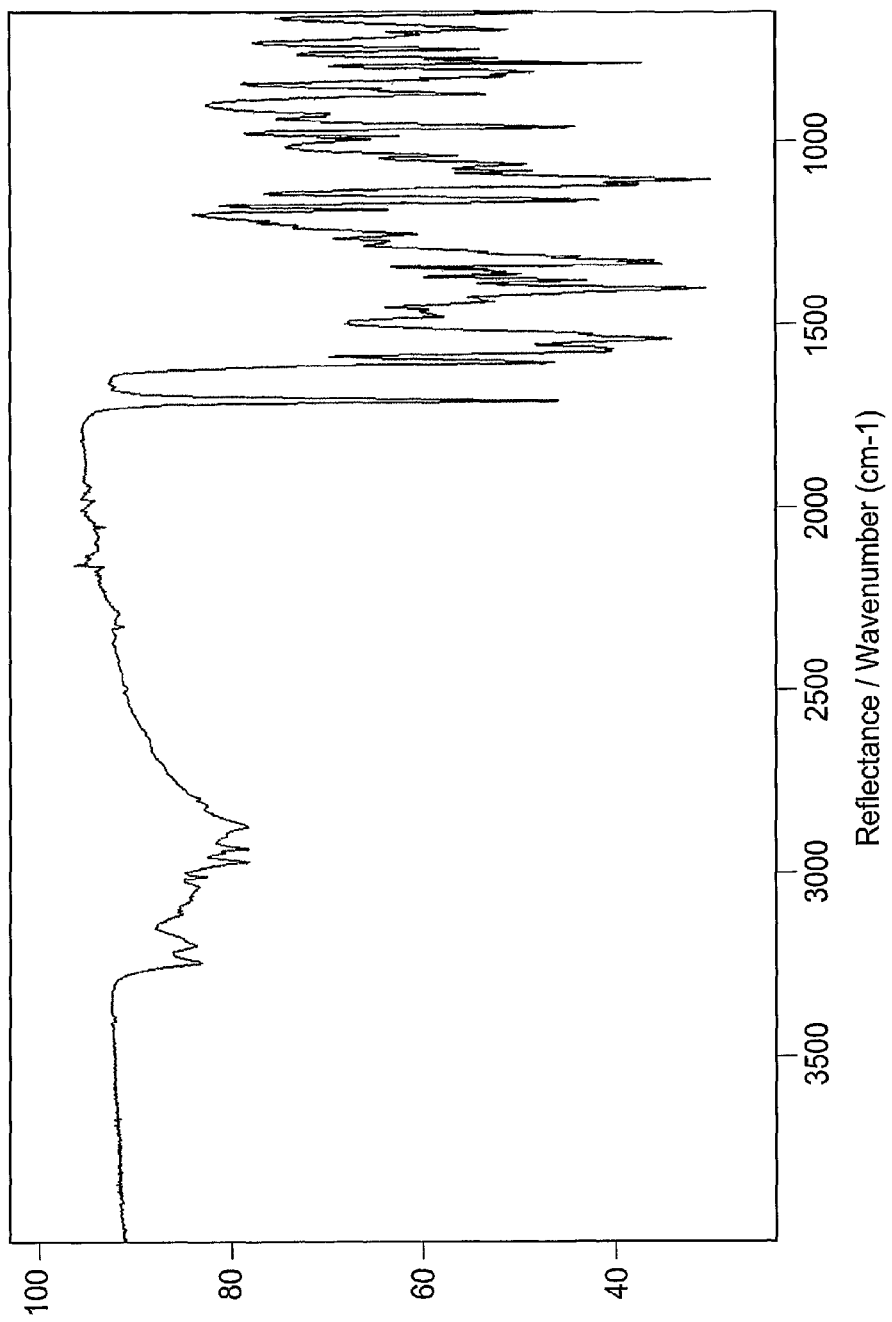
FIG. 8 shows an illustrative FT-IR spectrum for Form A.
Figure 9:
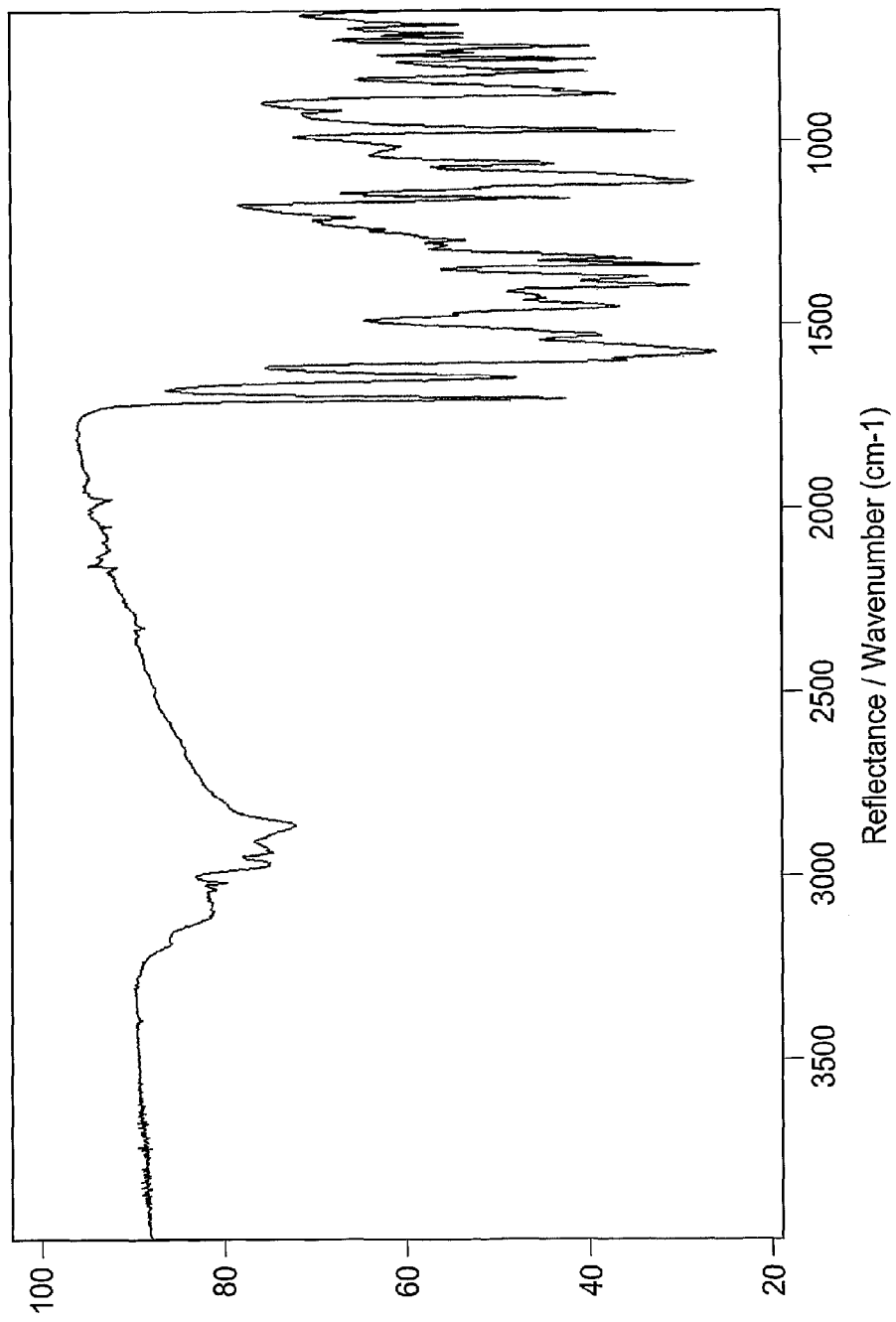
FIG. 9 shows an illustrative FT-IR spectrum for Form B.
Figure 10:
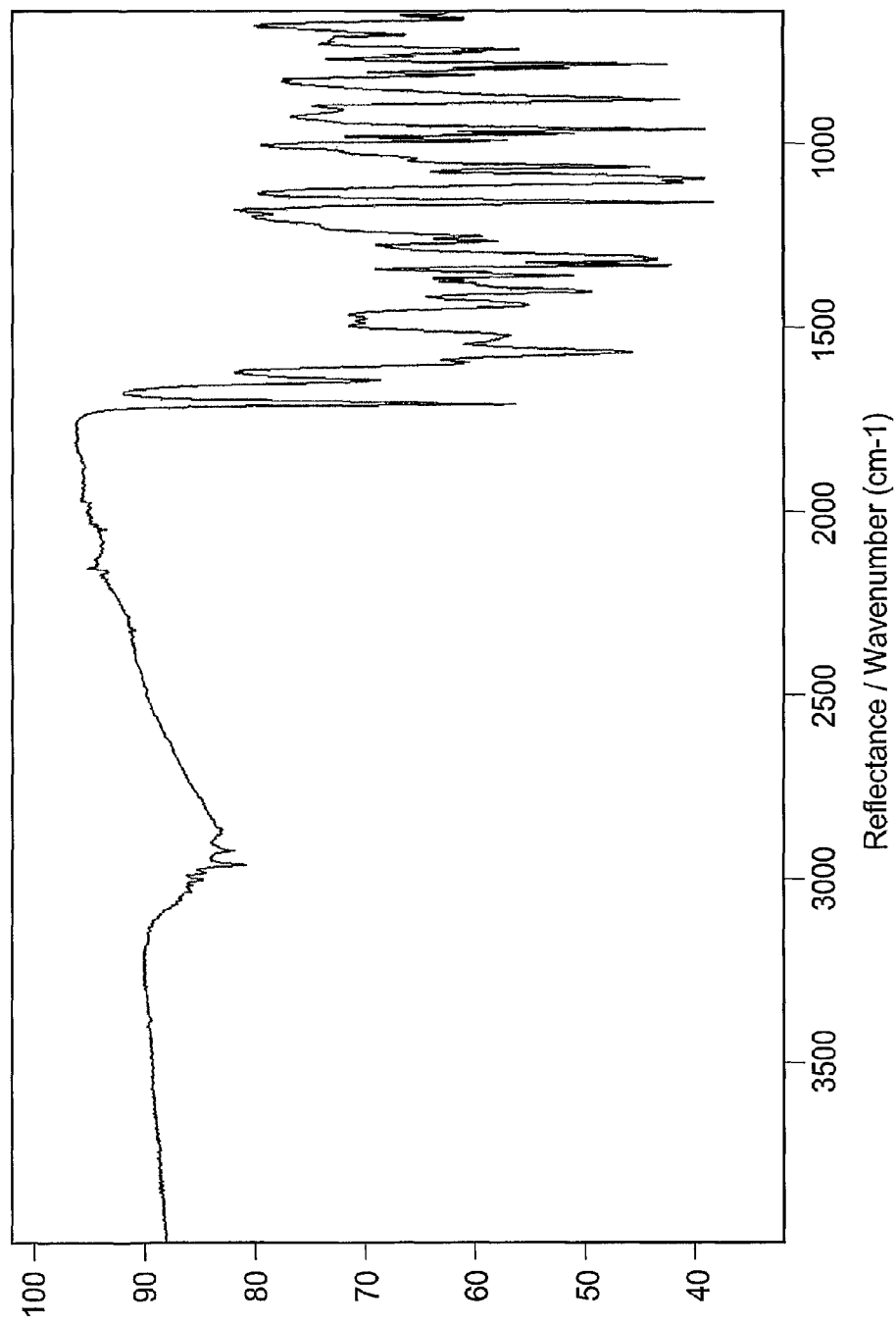
FIG. 10 shows an illustrative FT-IR spectrum for Form C.

Illustrative FT-IR spectra for Form A, Form B and Form C are shown in FIGS. 8, 9 and 10, respectively. Tables 4A, 4B and 4C list the corresponding unique and assignable absorption bands for Form A, Form B and Form C, respectively.

TABLE 4A

Form A FT-IR Spectroscopy Data

| Absorption Band[1] | Functional Group |
|---|---|
| 3247m[2], 3201m | NH stretch (amine and amide) |
| 1707s | C=O stretch (amide) |
| Region 1603-1524 (1603s, 1573m, 1540m) | C=C, C=N ring stretch and C—N—H bend (amide II/sulphonamide and amine) |
| 1334m, 1325w, 1314w | SO$_2$ asymmetric stretch |
| 1188m | |

TABLE 4A-continued

Form A FT-IR Spectroscopy Data

| Absorption Band[1] | Functional Group |
|---|---|
| 1120m | |
| 1085w | |
| 998w | |
| 933w | |
| 928w | |
| 831m | |
| 810m | |
| 775m | |
| 696m | |

[1]w: weak; m: medium; ms: medium-strong; s: strong
[2]Experimental error was ±3 cm$^{-1}$.

TABLE 4B

Form B FT-IR Spectroscopy Data

| Absorption Band[1] | Functional Group |
|---|---|
| 1704s | C=O stretch (amide) |
| 1646s | Acyclic C=N stretch |
| Region 1599-1530 (1599w, 1577s, 1530m) | C=C, C=N ring stretch and C—N—H bend (amide II/sulphonamide and amine) |
| 1452m | |
| 1395m | |
| 1338m, 1321m | SO$_2$ asymmetric stretch |
| 1211w | |
| 1112s | |
| 920w | |
| 781ms | |
| 722m | |
| 688m | |

[1]w: weak; m: medium; ms: medium-strong; s: strong

TABLE 4C

Form C FT-IR Spectroscopy Data

| Absorption Band[1] | Functional Group |
|---|---|
| 1707s | C=O stretch (amide) |
| 1644ms | Acyclic C=N stretch |
| Region 1596-1521, (1596w, 1521m) | C=C, C=N ring stretch and C—N—H bend (amide II/sulphonamide and amine) |
| 1333ms, 1320w, | SO$_2$ asymmetric stretch |
| 1313ms | |
| 1269m | |
| 909w | |
| 881s | |
| 797m | |
| 703m | |
| 661m | |

[1]w: weak; m: medium; ms: medium-strong; s: strong

Form A FT-IR

Form A has an FT-IR spectrum that comprises at least one absorption band selected from the group consisting of 696±2; 1085±2; 1188±2; 1540±2; and 3247±3 cm$^{-1}$. In one embodiment, Form A has an FT-IR spectrum that comprises an absorption band at 3247±3 cm$^{-1}$. In another embodiment, Form A has an FT-IR spectrum that comprises an absorption band at 3247±3 cm$^{-1}$, and further comprises at least one absorption band selected from the group consisting of 696±2; 1085±2; 1188±2; and 1540±2 cm$^{-1}$. In another embodiment, Form A has an FT-IR spectrum that comprises absorption bands at 3247±3 and 696±2 cm$^{-1}$. In another embodiment, Form A has an FT-IR spectrum that comprises absorption bands at 696±2; 1188±2; and 3247±3 cm$^{-1}$. In another embodiment, Form A has an FT-IR spectrum that comprises absorption bands at 696±2; 1188±2; 1540±2; and 3247±3 cm$^{-1}$. In another embodiment, Form A has an FT-IR spectrum that comprises absorption bands at 696±2; 1085±2; 1188±2; 1540±2; and 3247±3 cm$^{-1}$.

In another embodiment, Form A has an FT-IR spectrum that (a) comprises at least one absorption band selected from the group consisting of 696±2; 1085±2; 1188±2; 1540±2; and 3247±3 cm$^{-1}$, and (b) does not comprise an absorption band at 1645±2 cm$^{-1}$.

Form B FT-IR

Form B has an FT-IR spectrum that comprises at least one absorption band selected from the group consisting of 722±2; 920±2; 1211±2; 1395±2; and 1452±2 cm$^{-1}$. In another embodiment, Form B has an FT-IR spectrum that comprises an absorption band at 1452±2 cm$^{-1}$. In another embodiment, Form B has an FT-IR spectrum that comprises an absorption band at 1452±2 cm$^{-1}$, and further comprises at least one additional absorption band selected from the group consisting of 722±2; 920±2; 1211±2; and 1395±2 cm$^{-1}$. In another embodiment, Form B has an FT-IR spectrum comprising absorption bands at 1452±2 and 1395±2 cm$^{-1}$. In another embodiment, Form B has an IR spectrum comprising absorption bands at 1211±2; 1395±2; and 1452-±2 cm$^{-1}$. In another embodiment, Form B has an IR spectrum comprising absorption bands at 722±2; 1211±2; 1395±2; and 1452±2 cm$^{-1}$. In another embodiment, Form B has an IR spectrum comprising absorption bands at 722±2; 920±2; 1211±2; 1395-±2; and 1452±2 cm$^{-1}$.

In another embodiment, Form B has an FT-IR spectrum that (a) comprises at least one absorption band selected from the group consisting of 722±2; 920±2; 1211±2; 1395±2; and 1452±2 cm$^{-1}$, and (b) does not comprise an absorption band at 962±2 cm$^{-1}$.

Form C FT-IR

Form C has an FT-IR spectrum that comprises at least one absorption band selected from the group consisting of 661±2; 703±2; 797±2; 881±2; 909±2; and 1269±2 cm$^{-1}$. In another embodiment, Form C has an FT-IR spectrum that comprises an absorption band at 881±2 cm$^{-1}$. In another embodiment, Form C has an FT-IR spectrum that comprises an absorption band at 881±2 cm$^{-1}$, and further comprises at least one additional absorption band selected from the group consisting of 661±2; 703±2; 797±2; 909±2; and 1269±2 cm$^{-1}$. In another embodiment, Form C has an FT-IR spectrum comprising absorption bands at 881±2 and 661±2 cm$^{-1}$. In another embodiment, Form C has an FT-IR spectrum comprising absorption bands at 661±2; 797±2; and 881±2 cm$^{-1}$. In another embodiment, Form C has an FT-IR spectrum comprising absorption bands at 661±2; 703±2; 797±2; and 881±2 cm$^{-1}$. In another embodiment, Form C has an FT-IR spectrum comprising absorption bands at 661±2; 703±2; 797±2; 881±2; and 909±2 cm$^{-1}$. In another embodiment, Form C has an FT-IR spectrum comprising absorption bands at 661±2; 703±2; 797±2; 881±2; 909±2; and 1269±2 cm$^{-1}$.

In another embodiment, Form C has an FT-IR spectrum that (a) comprises at least one absorption band selected from the group consisting of 661±2; 703±2; 881±2; 909±2; and 1269±2 cm$^{-1}$, and (b) does not comprise an absorption band at 688±2 cm$^{-1}$. In another embodiment, Form C has an FT-IR spectrum that (a) comprises at least one absorption band Selected from the group consisting of 661±2; 703±2; 797±2; 881±2; 909±2; and 1269±2 cm$^{-1}$, and (b) does not comprise an absorption band at 696±2 cm$^{-1}$. In another embodiment, Form C has an FT-IR spectrum that (a) comprises at least one absorption band selected from the group consisting of 661±2; 703±2; 797±2; 881±2; 909±2; and 1269±2 cm$^{-1}$, and (b) does not comprise at least one absorption band selected from the group consisting of 688±2 or 696±2 cm$^{-1}$.

As previously noted, it is hypothesized that Form A crystallizes as Tautomer (1) and Form B and Form C each crystallize as Tautomer (2). FT-IR analysis supports this hypothesis. In particular, the Form C FT-IR spectrum shows a medium-strong absorption band at 1644±2 cm$^{-1}$ and the Form B FT-IR spectrum shows a strong absorption band at 1646±2 cm$^{-1}$. It is believed that these bands correspond to an acyclic C=N stretching frequency that is consistent with Tautomer (2). To the contrary, the Form A FT-IR spectrum shows no absorption band at the corresponding frequency. It is believed that Form A lacks an acyclic C=N stretching frequency because it crystallizes as Tautomer (1).

5. Fourier-Transform Raman Spectroscopy

Form A, Form B and Form C were each analyzed using Fourier-Transform Raman ("Raman") spectroscopy. Raman spectra for Form A, Form B and Form C were obtained using a ThermoNicolet 960 Raman spectrometer. Each sample (approximately 5 mg) was placed in a glass vial and exposed to 1064.5 nm Nd-YAG laser power for excitation. The data were collected at 2 cm$^{-1}$ resolution, measured as Raman intensity as a function of Raman shift. Data were processed as a Fourier Transform utilizing a Happ-Genzel apodization. Experimental error, unless otherwise noted, was ±2 cm$^{-1}$.

Figure 11:
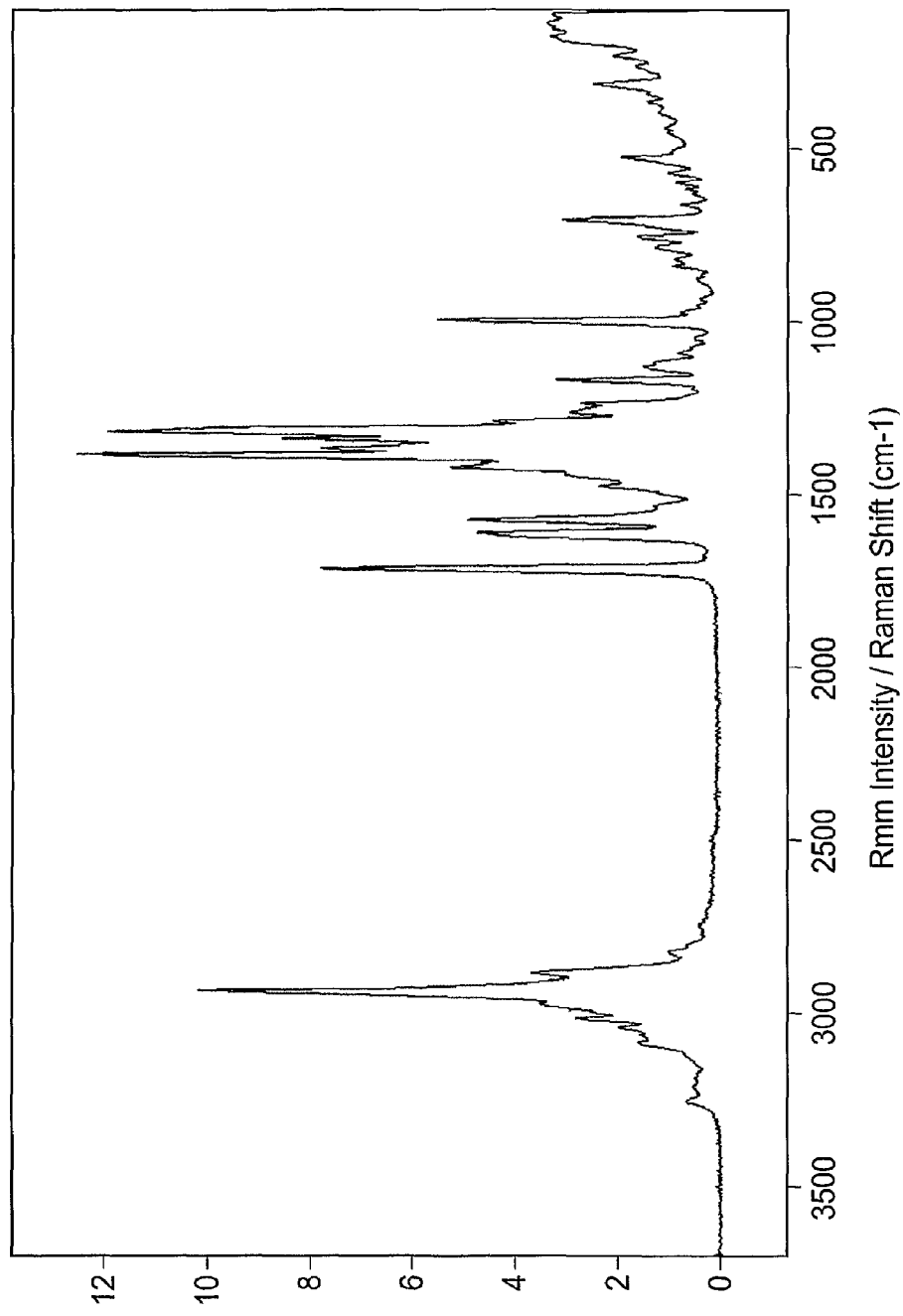
FIG. 11 shows an illustrative Raman spectrum for Form A.
Figure 12:
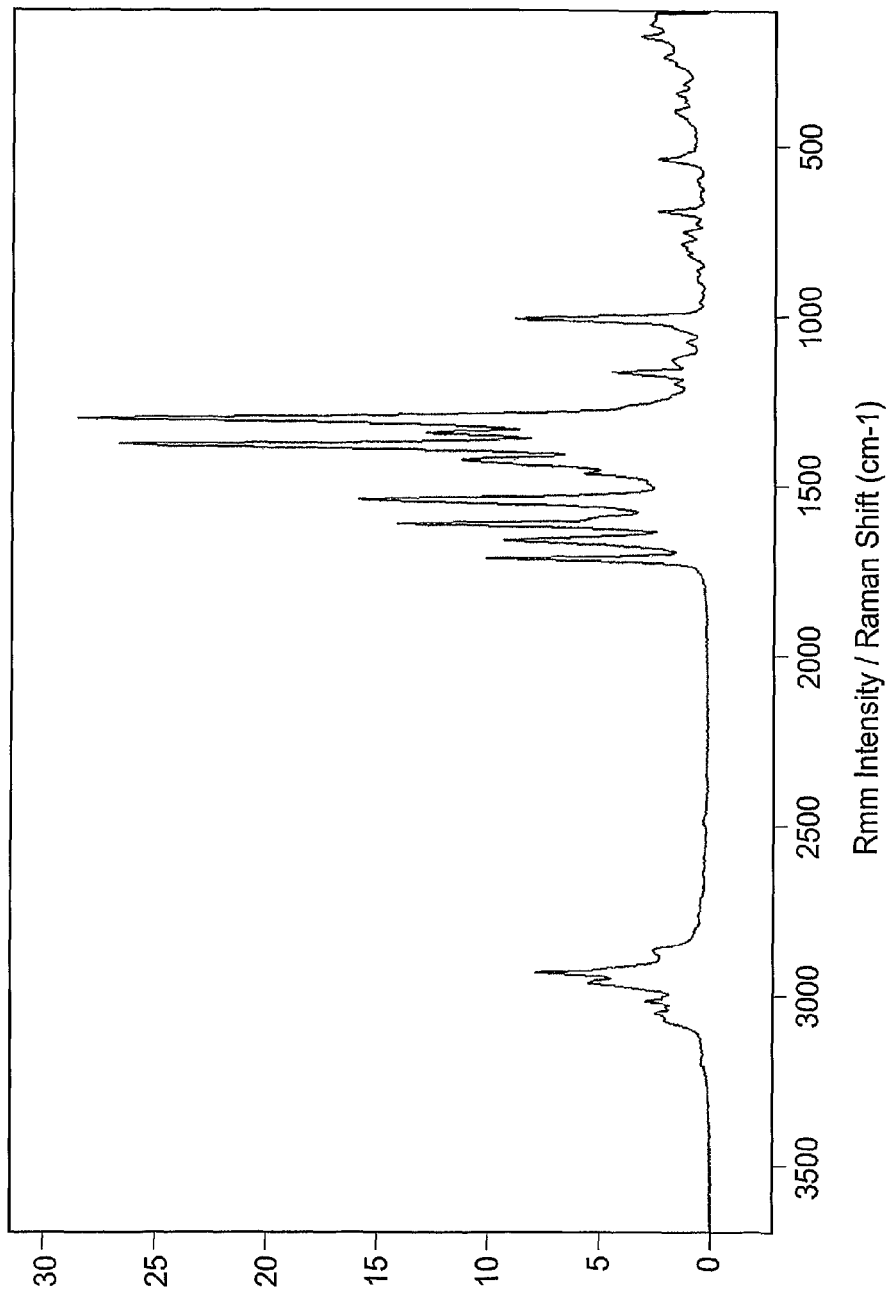
FIG. 12 shows an illustrative Raman spectrum for Form B.
Figure 13:
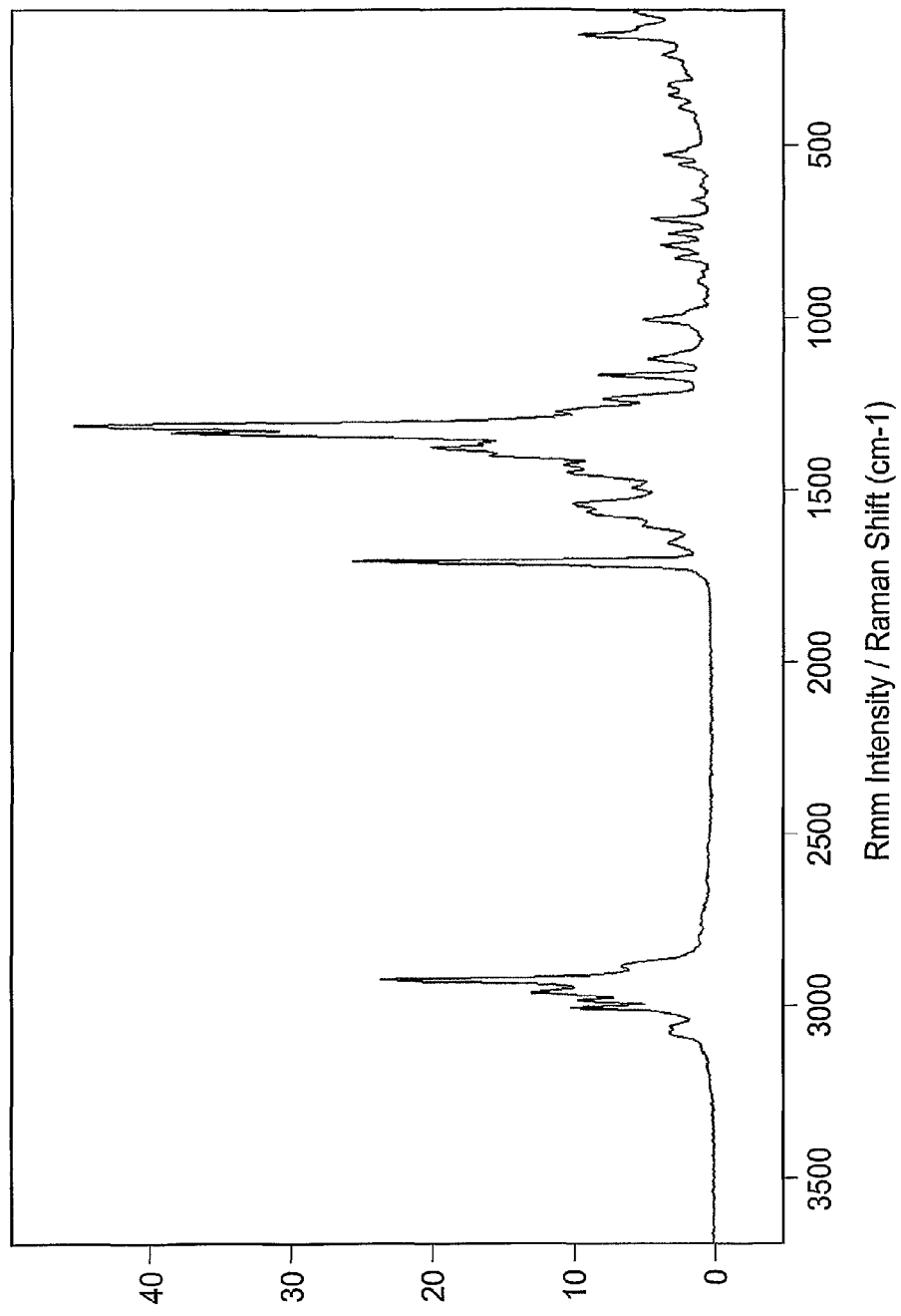
FIG. 13 shows an illustrative Raman spectrum for Form C.

Illustrative Raman spectra for Form A (measurement conditions: 2000 scans, laser Power: 750 mW, laser power at the sample: 400 mW), Form B (measurement conditions: 4000 scans, laser power: 600 mW, laser power at the sample: 340 mW), and Form C (measurement conditions: 960 scans, laser power: 600 mW, laser power at the sample: 340 mW) are shown in FIGS. 11, 12 and 13, respectively. The X-axis is Raman shift (cm$^{-1}$) and the Y-axis is intensity. The intensities are intensity assignments relative to the major absorption band in the spectrum and are not based on absolute values measured from the baseline. Tables 5A, 5B, and 5C list the corresponding characteristic Raman bands for Form A, Form B and Form C, respectively.

TABLE 5A

| Form A Raman Spectroscopy Data |
|---|
| Band[1] |
| 3255w[2] |
| 3040w |
| 3016m |
| 2937s |
| 2882m |
| 1711s |
| 1608m |
| 1569m |
| 1473w |
| 1418m |
| 1383s |
| 1364m |
| 1335m |
| 1316s |
| 1285w |
| 1259w |
| 1233m |
| 1165m |
| 993m |
| 752w |
| 701m |
| 521m |
| 310m |

[1] w: weak; m: medium; s: strong
[2] Experimental error was ±3 cm$^{-1}$.

TABLE 5B

Form B Raman Spectroscopy Data

| Band[1] |
|---|
| 3054w |
| 3020w |
| 2965w |
| 2936m |
| 2868m |
| 1706m |
| 1652m |
| 1605s |
| 1535s |
| 1456w |
| 1417m |
| 1376s |
| 1339m |
| 1299s |
| 1157m |
| 1000m |
| 689w |
| 536w |
| 173w |

[1]w: weak; m: medium; s: strong

TABLE 5C

Form C Raman Spectroscopy Data

| Band[1] |
|---|
| 3084w |
| 3065w |
| 3009m |
| 2988w |
| 2965m |
| 2930s |
| 2889w |
| 1707s |
| 1651w |
| 1561m |
| 1540m |
| 1447w |
| 1424w |
| 1397w |
| 1376s |
| 1336s |
| 1316s |
| 1269w |
| 1232w |
| 1161m |
| 1113w |
| 999w |
| 707w |
| 173m |

[1]w: weak; m: medium; s: strong

Form A Raman

Form A has a Raman spectrum that comprises at least one band selected from the group consisting of 993±2; 1383±2; 1473±2; 1569±2; and 3255±3 $cm^{-1}$. In another embodiment, Form A has a Raman spectrum that comprises a band at 3255±3 $cm^{-1}$. In another embodiment, Form A has a Raman spectrum that comprises a band at 3255±3 $cm^{-1}$, and further comprises at least one additional band selected from the group consisting of 993±2; 1383±2; 1473±2; and 1569±2 $cm^{-1}$. In another embodiment, Form A has a Raman spectrum that comprises bands at 1569±2 and 3255±3 $cm^{-1}$. In another embodiment, Form A has a Raman spectrum that comprises bands at 1473±2; 1569±2; and 3255±3 $cm^{-1}$. In another embodiment, Form A has a Raman spectrum that comprises bands at 1383±2; 1473±2; 1569±2; and 3255±3 $cm^{-1}$. In another embodiment, Form A has a Raman spectrum that comprises bands at 993±2; 1383±2; 1473±2; 1569±2; and 3255±3 $cm^{-1}$.

In another embodiment, Form A has a Raman spectrum that (a) comprises at least one band selected from the group consisting of 993±2; 1383±2; 1473±2; 1569±2; and 3255±3 $cm^{-1}$, and (b) does not comprise a band at 1652±2 $cm^{-1}$.

Form B Raman

Form B has a Raman spectrum that comprises at least one band selected from the group consisting of 689±2; 1299±2; 1456±2; and 1535±2 $cm^{-1}$. In another embodiment, Form B has a Raman spectrum that comprises a band at 1299±2 $cm^{-1}$. In another embodiment, Form B has a Raman spectrum that comprises a band at 1299±2 $cm^{-1}$, and further comprises at least one additional band selected from the group consisting of 689±2; 1456±2; and 1535±2 $cm^{-1}$. In another embodiment, Form B has a Raman spectrum comprising bands at 689±2 and 1299±2 $cm^{-1}$. In another embodiment, Form B has a Raman spectrum comprising bands at 689±2; 1299±2; and 1535±2 $cm^{-1}$. In another embodiment, Form B has a Raman spectrum comprising bands at 689±2; 1299±2; 1456±2; and 1535±2 $cm^{-1}$.

In another embodiment, Form B has a Raman spectrum that (a) comprises at least one band selected from the group consisting of 689±2; 1299±2; 1456±2; and 1535±2 $cm^{-1}$, and (b) does not comprise a band at 1316±2 $cm^{-1}$.

Form C Raman

Form C has a Raman spectrum that comprises at least one band selected from the group consisting of 707±2; 1447±2; and 2988±2 $cm^{-1}$. In another embodiment, Form C has a Raman spectrum that comprises a band at 2988±2 $cm^{-1}$. In another embodiment, Form C has a Raman spectrum with a significant band at 2988±2 $cm^{-1}$, and further comprises at least one additional band selected from the group consisting of 707±2 and 1447±2 $cm^{-1}$. In another embodiment, Form C has a Raman spectrum comprising bands at 707±2 and 2988±2 $cm^{-1}$. In another embodiment, Form C has a Raman spectrum comprising bands at 707±2; 1447±2; and 2988±2 $cm^{-1}$.

In another embodiment, Form C has a Raman spectrum that (a) comprises at least one band selected from the group consisting of 707±2; 1447±2; and 2988±2 $cm^{-1}$, and (b) does not comprise a band at 1417±2 $cm^{-1}$.

As previously noted, it is hypothesized that Form A crystallizes as Tautomer (1) and Form B and Form C each crystallize as Tautomer (2). FT-Raman analysis supports this hypothesis. In particular, the Form C FT-Raman spectrum shows a weak Raman band at 1651±2 $cm^{-1}$ and the Form B FT-Raman spectrum shows a medium Raman band at 1652±2 $cm^{-1}$. It is believed that these bands correspond to an acyclic C=N stretching frequency that is consistent with Tautomer (2). To the contrary, the Form A FT-Raman spectrum shows no Raman band at the corresponding frequency. It is believed that Form A lacks an acyclic C=N stretching frequency because it crystallizes as Tautomer (1).

C. PROPERTIES OF FORM A, FORM B AND FORM C

1. Thermodynamic Stability

Form A, Form B and Form C have different thermodynamic stabilities. Form B is more thermodynamically stable than Form A at ambient as well as elevated temperatures (see Example 13, below). Form B and Form C, however, are enantiotropically related. A crossover in the thermodynamic stability of Form B and Form C occurs at a temperature between about 40° C. and about 60° C. (see Example 14, below). In another embodiment, the crossover in the thermodynamic stability of Form B and Form C occurs at a temperature between about 40° C. and about 50° C. At temperatures above this crossover point, Form B is more thermodynamically stable than Form C. At temperatures below this crossover point (including at ambient temperatures), Form C is more thermodynamically stable than Form B.

These differences in thermodynamic stability have practical importance. The thermodynamic stability of a crystalline form affects the potential shelf life of a formulated pharmaceutical product comprising the crystalline form. Greater thermodynamic stability generally correlates with longer shelf life for the formulated pharmaceutical product. In addition, differences in thermodynamic stability can create issues where processing results in elevated temperatures (e.g., due to milling of the compound) or processing occurs over a range of temperatures. Such temperature changes during processing potentially can result in the conversion of one crystalline form into another crystalline form. If the resulting crystalline form is not the desired form, it may be necessary to more carefully control the processing temperature(s).

2. Morphology

Form A and Form B also have different crystal morphologies. Although factors such as temperature, solvent, impurities and hydrodynamics (vibrations) can affect crystal morphology, Form A and Form B clearly have distinct crystal morphologies. Form A typically exhibits a plate-like morphology. Form B typically exhibits a needle-like morphology. Form C comprises a mixture of laths, plates and fragments that range in size (maximum dimension) from about 5 microns to about 350 microns; typically 50 to 60 microns.

These differences in morphology potentially can affect the ease of processing the compound to prepare a formulated pharmaceutical product. For example, a needle-like morphology can make filtration and processing more difficult. Alternatively, a plate-like morphology often is more equi-dimensional resulting in improved flow and handling of the compound thereby improving the ease of filtration, processing and tableting steps relative to a needle-like morphology.

3. Color

Form A, Form B and Form C also have different visual appearances. Form A typically has a slightly yellowish to ivory coloration. Form B typically has a yellow coloration. Form C typically has a light yellow coloration. The product specification for a formulated pharmaceutical product often specifies not only the chemical purity of the active ingredient, but also the phase purity of the active ingredient. Batch-to-batch variability in the crystalline form of an active ingredient generally is not desirable. In the case of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, the color of a batch can be used for quality control purposes to provide a qualitative means of assessing whether the phase purity of that batch satisfies the desired phase purity standard. In addition, product aesthetics are important and uniformity of color in the final pharmaceutical product appearance is desirable. Where the color properties of a crystalline form affect the appearance of the formulated product, appropriate control of the crystalline form present in the product will need to be exercised to maintain color consistency for the product.

D. ADDITIONAL EMBODIMENTS

The following are additional embodiments of Form A, Form B and Form C:

Additional Embodiments of Form A

In one embodiment, Form A has a PXRD pattern comprising a diffraction peak at 8.5±0.1 degrees two theta, and an FT-IR spectrum comprising an absorption band at 3247±3 cm$^{-1}$. In another embodiment, Form A has a PXRD pattern comprising a diffraction peak at 8.5±0.1 degrees two theta, and a FT-IR spectrum comprising absorption bands at 3247±3 and 696±2 cm$^{-1}$. In another embodiment, Form A has a PXRD pattern comprising diffraction peaks at 8.5±0.1 and 9.0±0.1 degrees two theta, and a FT-IR spectrum comprising an absorption band at 3247±3 cm$^{-1}$. In another embodiment, Form A has a PXRD pattern comprising diffraction peaks at 8.5±0.1 and 9.0±0.1 degrees two theta, and a FT-IR spectrum comprising absorption bands at 696±2 cm$^{-1}$ and 3247±3 cm$^{-1}$. In another embodiment, Form A has a PXRD pattern comprising diffraction peaks at 8.5±0.1; 9.0±0.1; and 16.9±0.1 degrees two theta, and a FT-IR spectrum comprising absorption bands at 696±2; 1188±2; and 3247±3 cm$^{-1}$.

In another embodiment, Form A has a PXRD pattern comprising a diffraction peak at 8.5±0.1 degrees two theta, and a Raman spectrum comprising a band at 3255±3 cm$^{-1}$. In another embodiment, Form A has a PXRD pattern comprising a diffraction peak at 8.5±0.1 degrees two theta, and a Raman spectrum comprising bands at 1569±2 and 3255±3 cm$^{-1}$. In another embodiment, Form A has a PXRD pattern comprising diffraction peaks at 8.5±0.1 and 9.0±0.1 degrees two theta, and a Raman spectrum comprising a band at 3255±3 cm$^{-1}$. In another embodiment, Form A has a PXRD pattern comprising diffraction peaks at 8.5±0.1 and 9.0±0.1 degrees two theta, and a Raman spectrum comprising bands at 1569±2 and 3255±3 cm$^{-1}$. In another embodiment, Form A has a PXRD pattern comprising diffraction peaks at 8.5±0.1; 9.0±0.1; and 16.9±0.1 degrees two theta, and a Raman spectrum comprising bands at 1569±2 and 3255±3 cm$^{-1}$. In another embodiment, Form A has a PXRD pattern comprising diffraction peaks at 8.5±0.1; 9.0±0.1; and 16.9±0.1 degrees two theta, and a Raman spectrum comprising bands at 1473±2; 1569±2; 3255±3 and cm$^{-1}$.

In another embodiment, Form A has a PXRD pattern comprising a diffraction peak at 8.5±0.1 degrees two theta, and a melting point of 174° C.±3° C. In another embodiment, Form A has a PXRD pattern comprising diffraction peaks at 8.5±0.1 and 9.0±0.1 degrees two theta, and a melting point of 174° C.±3° C. In another embodiment, Form A has a PXRD pattern comprising diffraction peaks at 8.5±0.1; 9.0±0.1; and 16.9±0.1 degrees two theta, and a melting point of 174° C.±3° C.

In another embodiment, Form A has a PXRD pattern comprising a diffraction peak at 8.5±0.1 degrees two theta, a FT-IR spectrum comprising an absorption band at 3247±3 cm$^{-1}$ and a melting point of 174° C.±3° C. In another embodiment, Form A has a PXRD pattern comprising diffraction peaks at 8.5±0.1 and 9.0±0.1 degrees two theta, a FT-IR spectrum comprising an absorption band at 3247±3 cm$^{-1}$ and a melting point of 174° C.±3° C. In another embodiment, Form A has a PXRD pattern comprising diffraction peaks at 8.5±0.1; 9.0±0.1; and 16.9±0.1 degrees two theta, a FT-IR spectrum comprising absorption bands at 3247±3 and 696±2 cm$^{-1}$ and a melting point of 174° C.±3° C. In another embodiment, Form A has an PXRD pattern comprising diffraction peaks at 8.5±0.1; 9.0±0.1; and 16.9±0.1 degrees two theta, a FT-IR spectrum comprising absorption bands at 696±2; 1188±2; and 3247±3 cm$^{-1}$, and a melting point of 174° C.±3° C.

In another embodiment, Form A has a PXRD pattern comprising a diffraction peak at 8.5±0.1 degrees two theta, a FT-IR spectrum comprising an absorption band at 3247±3 cm$^{-1}$, and a Raman spectrum comprising a band at 3255±3 cm$^{-1}$. In another embodiment, Form A has a PXRD pattern comprising diffraction peaks at 8.5±0.1 and 9.0±0.1 degrees two theta, a FT-IR spectrum comprising absorption bands at 696±2 and 3247±3 cm$^{-1}$, and a Raman spectrum comprising bands at 1569±2 and 3255±3 cm$^{-1}$. In another embodiment, Form A has a PXRD pattern comprising diffraction peaks at 8.5±0.1; 16.9±0.1; and 22.5±0.1, degrees two theta, a FT-IR spectrum comprising absorption bands at 696±2; 1188±2 and 3247±3 cm$^{-1}$, and a Raman spectrum comprising bands at 1569±2 and 3255±3 cm$^{-1}$.

In another embodiment, Form A has a PXRD pattern comprising diffraction peaks at 8.5±0.1 and 9.0±0.1 degrees two theta, an FT-IR spectrum comprising absorption bands at 696±2 and 3247±3 cm$^{-1}$, an Raman spectrum comprising bands at 1569±2 and 3255±3 cm$^{-1}$, and a melting point of 174° C.±3° C. In another embodiment, Form A has a PXRD pattern comprising diffraction peaks at; 8.5±0.1; 16.9±0.1; and 22.5±0.1 degrees two theta, an FT-IR spectrum comprising absorption bands at 696±2; 1188±2; and 3247±3; cm$^{-1}$, an Raman spectrum comprising bands at 1569±2 and 3255±3 cm$^{-1}$, and a melting point of 174° C.±3° C.

Additional Embodiments of Form B

In one embodiment, Form B has a PXRD pattern comprising a diffraction peak at 3.6±0.1 degrees two theta and FT-IR spectrum comprising an absorption bands at 1452±2 cm$^{-1}$. In another embodiment, Form B has a PXRD pattern comprising a diffraction peak at 3.6±0.1 degrees two theta and FT-IR spectrum comprising absorption bands at 1395±2 and 1452±2 cm$^{-1}$. In another embodiment, Form B has a PXRD pattern comprising a diffraction peak at 3.6±0.1 degrees two theta and FT-IR spectrum comprising absorption bands at 1211±2; 1395±2 and 1452±2 cm$^{-1}$. In another embodiment, Form B has a PXRD pattern comprising a diffraction peak at 3.6±0.1 degrees two theta and FT-IR spectrum comprising absorption bands at 722±2; 920±2; 1211±2; 1395±2 and 1452±2 cm$^{-1}$. In another embodiment, Form B has an a PXRD pattern comprising diffraction peaks at 3.6±0.1 and 7.2±0.1 degrees two theta and FT-IR spectrum comprising absorption bands at 1211±2; 1395±2; and 1452±2 cm$^{-1}$.

In one embodiment, Form B has a PXRD pattern comprising a diffraction peak at 3.6±0.1 degrees two theta and a melting point of 218° C.±3° C. In another embodiment, Form B has a PXRD pattern comprising diffraction peaks at 3.6±0.1 and 7.2±0.1 degrees two theta, and a melting point of 218° C.±3° C. In another embodiment, Form B has a PXRD pattern comprising diffraction peaks at 3.6±0.1; 7.2±0.1; and 23.8±0.1 degrees two theta, and a melting point of 218° C.±3° C. In another embodiment, Form B has a PXRD pattern comprising diffraction peaks at 3.6±0.1; 7.2±0.1; 10.1±0.1; 14.4±0.1; and 23.8±0.1 degrees two theta, and a melting point of 218° C.±3° C.

In another embodiment, Form B has a PXRD pattern comprising a diffraction peak at 3.6±0.1 degrees two theta, an FT-IR spectrum comprising an absorption band at 1452±2 cm$^{-1}$ and a melting point of 218° C.±3° C. In another embodiment, Form B has a PXRD pattern comprising a diffraction peak at 3.6±0.1 degrees two theta, an FT-IR spectrum comprising absorption bands at 1395±2 cm$^{-1}$ and 1452±2 cm$^{-1}$ and a melting point of 218° C.±3° C. In another embodiment, Form B has a PXRD pattern comprising diffraction peaks at 3.6±0.1; 7.2±0.1; 10.1±0.1; 14.4±0.1; and 23.8±0.1 degrees two theta, a FT-IR spectrum comprising absorption bands at 722±2; 920±2; 1211±2; 1395±2; and 1452±2 cm$^{-1}$ and a melting point of 218° C.±3° C.

In another embodiment, Form B has a PXRD pattern comprising a diffraction peak at 3.6±0.1 degrees two theta, and a Raman spectrum comprising an absorption band at 1299±2 cm$^{-1}$. In another embodiment, Form B has a PXRD pattern comprising a diffraction peak at 3.6±0.1 degrees two theta, and a Raman spectrum comprising absorption bands at 689±2 and 1299±2 cm$^{-1}$. In another embodiment, Form B has a PXRD pattern comprising a peak at 3.6±0.1 degrees two theta, and a Raman spectrum comprising absorption bands at 689±2; 1299±2; and 1535±2 cm$^{-1}$. In another embodiment, Form B has a PXRD pattern comprising a diffraction peak at 3.6±0.1 degrees two theta, and an Raman spectrum comprising absorption bands at 689±2; 1299±2; 1456±2; and 1535±2 cm$^{-1}$.

In another embodiment, Form B has a PXRD pattern comprising a diffraction peak at 3.6±0.1 degrees two theta, a FT-IR spectrum comprising an absorption band at 1452±2 cm$^{-1}$, and a Raman spectrum comprising an absorption band at 1299±2 cm$^{-1}$. In another embodiment, Form B has a PXRD pattern comprising a diffraction peak at 3.6±0.1 degrees two theta, an FT-IR spectrum comprising absorption bands at 1395±2 cm$^{-1}$ and 1452±2 cm$^{-1}$, and a Raman spectrum comprising a absorption bands at 1299±2 and 689±2 cm$^{-1}$. In another embodiment, Form B has a PXRD pattern comprising a diffraction peak at 3.6±0.1 degrees two theta, a FT-IR spectrum comprising absorption bands at 1395±2 cm$^{-1}$; 1452±2; and 1535±2 cm$^{-1}$, and a Raman spectrum comprising a absorption bands at 1299±2 and 689±2 cm$^{-1}$.

In another embodiment, Form B has a PXRD pattern comprising a diffraction peak at 3.6±0.1 degrees two theta, an FT-IR spectrum comprising absorption bands at 1395±2 cm$^{-1}$ and 1452±2 cm$^{-1}$, a Raman spectrum comprising an absorption band at 1299±2 cm$^{-1}$ and a melting point of 218° C.±3° C. In another embodiment, Form B has a PXRD pattern comprising a diffraction peak at 3.6±0.1 degrees two theta, an FT-IR spectrum comprising absorption bands at 1395±2 cm$^{-1}$; 1452±2; and 1535±2 cm$^{-1}$, a Raman spectrum comprising a absorption bands at 1299±2 and 689±2 cm$^{-1}$ and a melting point of 218° C.±3° C.

Additional Embodiments of Form C

In another embodiment, Form C has a PXRD pattern comprising a diffraction peak at 6.7±0.1 degrees two theta and a FT-IR spectrum comprising an absorption band at 881±2 cm$^{-1}$. In another embodiment, Form C has a PXRD pattern comprising a diffraction peak at 6.7±0.1 degrees two theta and a FT-IR spectrum comprising an absorption band at 881±2 cm$^{-1}$ and 661±2 cm$^{-1}$. In another embodiment, Form C has a PXRD pattern comprising a diffraction peak at 6.7±0.1 degrees two theta and a FT-IR spectrum comprising an absorption band at 881±2; 797±2; 703±2; and 661±2 cm$^{-1}$. In another embodiment, Form C has a PXRD pattern comprising a diffraction peak at 6.7±0.1 and 26.1±0.1 degrees two theta and a FT-IR spectrum comprising an absorption band at 881±2 cm$^{-1}$ and 661±2 cm$^{-1}$.

In another embodiment, Form C has a PXRD pattern comprising a diffraction peak at 6.7±0.1 degrees two theta and a melting point of 188° C.±3° C. In another embodiment, Form C has a PXRD pattern comprising diffraction peaks at 6.7±0.1 and 26.1±0.1 degrees two theta and a melting point of 188° C.±3° C. In another embodiment, Form C has a PXRD pattern comprising diffraction peaks at 6.7±0.1; 20.2±0.1; and 17.7±0.1 degrees two theta and a melting point of 188° C.±3° C. In another embodiment, Form C has a PXRD pattern comprising diffraction peaks at 6.7±0.1; 10.6±0.1; 14.0±0.1; 17.7±0.1; and 20.2±0.1 degrees two theta and a melting point of 188° C.±3° C.

In another embodiment, Form C has a PXRD pattern comprising a diffraction peak at 6.7±0.1 degrees two theta and a Raman spectrum comprising an absorption band at 2988±2 cm$^{-1}$. In another embodiment, Form C has a PXRD pattern comprising a diffraction peak at 6.7±0.1 degrees two theta and a Raman spectrum comprising absorption bands at 707±2 and 2988±2 cm$^{-1}$. In another embodiment, Form C has a PXRD pattern comprising a diffraction peak at 6.7±0.1 degrees two theta and a Raman spectrum comprising absorption bands at 707±2; 1447±2; and 2988±2 cm$^{-1}$. In another embodiment, Form C has a PXRD pattern comprising diffraction peaks at 6.7±0.1 and 26.1±0.1 degrees two theta and a Raman spectrum comprising absorption bands at 707±2; 1447±2; and 2988±2 cm$^{-1}$.

In another embodiment, Form C has a PXRD pattern comprising a diffraction peak at 6.7±0.1 degrees two theta, a FT-IR spectrum comprising absorption bands at 661±2 cm$^{-1}$ and 881±2 cm$^{-1}$ and a melting point of 188° C.±3° C. In another embodiment, Form C has a PXRD pattern comprising diffraction peaks at 6.7±0.1 and 20.2±0.1 degrees two theta, a FT-IR spectrum comprising absorption bands at 661±2, 881±2 and 797±2 cm$^{-1}$ and a melting point of 188° C.±3° C.

In another embodiment, Form C has a PXRD pattern comprising a diffraction peak at 6.7±0.1 degrees two theta, a FT-IR spectrum comprising an absorption band at 881±2 cm$^{-1}$, an Raman spectrum comprising an absorption band at 2988±2 cm$^{-1}$ and a melting point of 188° C.±3° C. In another embodiment, Form C has a PXRD pattern comprising a diffraction peak at 6.7±0.1 degrees two theta, a FT-IR spectrum comprising absorption bands at 661±2 cm$^{-1}$ and 881±2 cm$^{-1}$, an Raman spectrum comprising an absorption band at 2988±2 cm$^{-1}$ and a melting point of 188° C.±3° C. In another embodiment, Form C has a PXRD pattern comprising diffraction peaks at 6.7±0.1 and 20.2±0.1 degrees two theta, a FT-IR spectrum comprising absorption bands at 661±2 cm$^{-1}$ and 881±2 cm$^{-1}$, an Raman spectrum comprising absorption bands at 707±2 and 2988±2 cm$^{-1}$ and a melting point of 188° C.±3° C. In another embodiment, Form C has a PXRD pattern comprising diffraction peaks at 6.7±0.1 and 20.2±0.1 degrees two theta, a FT-IR spectrum comprising absorption bands at 881±2; 797±1; 703±2; and 661±2 cm$^{-1}$, an Raman spectrum comprising absorption bands at 707±2; 1447±2 and 2988±2 cm$^{-1}$ and a melting point of 188° C.±3° C.

E. PHASE PURE FORMS AND COMBINATIONS OF FORM A, FORM B, AND FORM C

Each of Form A, Form B, and Form C can be obtained as a substantially phase pure form. Alternatively, each of Form A, Form B, and Form C can be present in combination with one or more of the other forms.

In one embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 50% by weight of the compound is Form A. In additional embodiments, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 20%, at least about 30%, or at least about 40% by weight of the compound is Form A. In additional embodiments, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 60%, at least about 70%, at least about 80%, at least about 85%, at least about 90%, at least about 95%, at least about 96%, at least about 97%, at least about 98%, or at least about 99% by weight of the compound is Form A. In another embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form A.

In one embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 50% by weight of the compound is Form B. In additional embodiments, the invention comprises N—O-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 20%, at least about 30%, or at least about 40% by weight of the compound is Form B. In additional embodiments, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 60%, at least about 70%, at least about 80%, at least about 85%, at least about 90%, at least about 95%, at least about 96%, at least about 97%, at least about 98%, or at least about 99% by weight of the compound is Form B. In another embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form B.

In one embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 50% by weight of the compound is Form C. In additional embodiments, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 20%, at least about 30%, or at least about 40% by weight of the compound is Form C. In additional embodiments, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide, wherein at least about 60%, at least about 70%, at least about 80%, at least about 85%, at least about 90%, at least about 95%, at least about 96%, at least about 97%, at least about 98%, or at least about 99% by weight of the compound is Form C. In another embodiment, the invention comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form C.

F. METHODS FOR PREPARING FORM A, FORM B, AND FORM C

The present invention also comprises methods for preparing Form A, Form B, and Form C. Representative methods are disclosed in the examples contained in this application.

The invention further comprises each of Form A, Form B, and Form C prepared in accordance with the methods disclosed in this application. In one embodiment, the invention comprises Form A prepared in accordance with such methods. In another embodiment, the invention comprises Form B prepared in accordance with such methods. In another embodiment the invention comprises Form C prepared in accordance with such methods.

G. PHARMACEUTICAL COMPOSITIONS

Form A, Form B, and Form C and combinations of such forms can be administered by any suitable route, preferably in the form of a pharmaceutical composition adapted to such a route, and in a dose effective for the treatment intended. Accordingly, the invention specifically comprises pharmaceutical compositions comprising at least one anhydrous crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide in association with one or more pharmaceutically-acceptable carriers. The amount of Form A, Form B, and/or Form C that is administered and the dosage regimen for treating a condition or disorder with Form A, Form B, and/or Form C depends on a variety of factors, including the age, weight, sex and medical condition of the subject, the severity of the disease, the route and frequency of administration, and the particular compound employed, and thus may vary widely. The pharmaceutical compositions may contain Form A, Form B, and/or Form C in the range of about 0.1 to 2000 mg, preferably in the range of about 0.5 to 500 mg and most preferably between about 1 and 200 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In one embodiment, the pharmaceutical composition comprises Form A and a pharmaceutically-acceptable carrier. In another embodiment, the pharmaceutical composition comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form A, and a pharmaceutically-acceptable carrier. In another embodiment, the pharmaceutical composition comprises Form B and a pharmaceutically-acceptable carrier. In another embodiment, the pharmaceutical composition comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form B, and a pharmaceutically-acceptable carrier. In another embodiment, the pharmaceutical composition comprises Form C and a pharmaceutically-acceptable carrier. In another embodiment, the pharmaceutical composition comprises N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide that is substantially phase pure Form C, and a pharmaceutically-acceptable carrier.

In yet another embodiment, the pharmaceutical composition comprises a combination of at least two forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide selected from the group consisting of Form A, Form B, and Form C and a pharmaceutically-acceptable carrier. In one embodiment, the weight ratio of the amount of the first form to the second form is at least about 1:1. In other embodiments, this ratio is at least about 3:2; at least about 7:3; at least about 4:1; at least about 9:1; at least about 95:5; at least about 96:4; at least about 97:3; at least about 98:2; or at least about 99:1. In another embodiment, the pharmaceutical composition comprises three forms of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide selected from the group consisting of Form A, Form B, and Form C and a pharmaceutically-acceptable carrier.

H. METHODS OF TREATMENT

The present invention further comprises methods for treating a condition in a subject having or susceptible to having such a condition, by administering to the subject a therapeutically-effective amount of one or more compounds of Form A, Form B, Form C or combinations of such forms as described above. In one embodiment, the treatment is preventative treatment. In another embodiment, the treatment is palliative treatment. In another embodiment, the treatment is restorative treatment.

The conditions that can be treated in accordance with the present invention are PDE-5 mediated conditions. Such conditions include cardiovascular diseases, metabolic diseases, central nervous system diseases, pulmonary diseases, sexual dysfunction, and renal dysfunction.

In one embodiment, the condition is a cardiovascular disease, particularly a cardiovascular disease selected from the group consisting of hypertension (such as essential hypertension, pulmonary hypertension, secondary hypertension, isolated systolic hypertension, hypertension associated with diabetes, hypertension associated with atherosclerosis, and renovascular hypertension); complications associated with hypertension (such as vascular organ damage, congestive heart failure, angina, stroke, glaucoma and impaired renal function); valvular insufficiency; stable, unstable and variant (Prinzmetal) angina; peripheral vascular disease; myocardial infarct; stroke; thromboembolic disease; restenosis; arteriosclerosis; atherosclerosis; pulmonary arterial hypertension; angiostenosis after bypass; angioplasty (such as percutaneous transluminal angioplasty, or percutaneous transluminal coronary angioplasty); hyperlipidemia; hypoxic vasoconstriction; vasculitis, such as Kawasaki's syndrome; heart failure (such as congestive, decompensated, systolic, diastolic and left ventricular heart failure; right ventricular heart failure; and left ventricular hypertrophy); Raynaud's disease; preeclampsia; pregnancy-induced high blood pressure; cardiomyopathy; and arterial occlusive disorders.

In another embodiment, the condition is hypertension. In another embodiment, the condition is pulmonary arterial hypertension. In another embodiment, the condition is heart failure. In another embodiment, the condition is diastolic heart failure. In another embodiment, the condition is systolic heart failure. In another embodiment, the condition is angina. In another embodiment, the condition is thrombosis. In another embodiment, the condition is stroke.

In another embodiment, the condition is a metabolic disease, particularly a metabolic disease selected from the group consisting of Syndrome X; insulin resistance or impaired glucose tolerance; diabetes (such as type I and type II diabetes); syndromes of insulin resistance (such as insulin receptor disorders, Rabson-Mendenhall syndrome, leprechaunism, Kobberling-Dunnigan syndrome, Seip syndrome, Lawrence syndrome, Cushing syndrome, acromegaly, pheochomocytoma, glucagonoma, primary aldosteronism, somatostatinoma, Lipoatrophic diabetes, β-cell toxin induced diabetes, Grave's disease, Hashimoto's thyroiditis and idiopathic Addison's disease); diabetic complications (such as diabetic gangrene, diabetic arthropathy, diabetic nephropathy, diabetic glomerulosclerosis, diabetic deramatopathy, diabetic neuropathy, peripheral diabetic neuropathy, diabetic cataract, and diabetic retinopathy); hyperglycemia; and obesity.

In another embodiment, the condition is insulin resistance. In another embodiment, the condition is nephropathy.

In another embodiment, the condition is a disease of the central nervous system, particularly a disease of the central nervous system selected from the group consisting of vascular dementia; craniocerebral trauma; cerebral infarcts; dementia; concentration disorders; Alzheimer's disease; Parkinson's disease; amyolateral sclerosis (ALS); Huntington's disease; multiple sclerosis; Creutzfeld-Jacob; anxiety; depression; sleep disorders; and migraine. In one embodiment, the condition is Alzheimer's disease. In another embodiment, the condition is Parkinson's disease. In one embodiment, the condition is ALS. In another embodiment, the condition is a concentration disorder.

In one embodiment, the condition is a pulmonary disease, particularly a pulmonary disease selected from the group consisting of asthma; acute respiratory distress; cystic fibrosis; chronic obstructive pulmonary disease (COPD); bronchitis; and chronic reversible pulmonary obstruction.

In one embodiment, the condition is sexual dysfunction, particularly sexual dysfunction selected from the group consisting of impotence (organic or psychic); male erectile dysfunction; clitoral dysfunction; sexual dysfunction after spinal cord injury; female sexual arousal disorder; female sexual orgasmic dysfunction; female sexual pain disorder; and female hypoactive sexual desire disorder. In another embodiment, the condition is erectile dysfunction.

In another embodiment, the condition is renal dysfunction, particularly a renal dysfunction selected from the group consisting of acute or chronic renal failure; nephropathy (such as diabetic nephropathy); glomerulopathy; and nephritis.

In another embodiment, the condition is pain. In another embodiment, the condition is acute pain. Examples of acute pain include acute pain associated with injury or surgery. In another embodiment, the condition is chronic pain. Examples of chronic pain include neuropathic pain (including postherpetic neuralgia and pain associated with peripheral, cancer or diabetic neuropathy), carpal tunnel syndrome, back pain (including pain associated with herniated or ruptured intervertabral discs or abnormalities of the lumber facet joints, sacroiliac joints, paraspinal muscles or the posterior longitudinal ligament), headache, cancer pain (including tumour related pain such as bone pain, headache, facial pain or visceral pain) or pain associated with cancer therapy (including postchemotherapy syndrome, chronic postsurgical pain syndrome, post radiation syndrome, pain associated with immunotherapy, or pain associated with hormonal therapy), arthritic pain (including osteoarthritis and rheumatoid arthritis pain), chronic post-surgical pain, post herpetic neuralgia, trigeminal neuralgia, HIV neuropathy, phantom limb pain, central post-stroke pain and pain associated with chronic alcoholism, hypothyroidism, uremia, multiple sclerosis, spinal cord injury, Parkinson's disease, epilepsy and vitamin deficiency. In another embodiment, the condition is nociceptive pain (including pain from central nervous system trauma, strains/sprains, burns, myocardial infarction and acute pancreatitis, post-operative pain (pain following any type of surgical procedure), posttraumatic pain, renal colic, cancer pain and back pain). In another embodiment, the condition is pain associated with inflammation (including arthritic pain (such as osteoarthritis and rheumatoid disease pain), ankylosing spondylitis, visceral pain (including inflammatory bowel disease, functional bowel disorder, gastro-esophageal reflux, dyspepsia, irritable bowel syndrome, functional abdominal pain syndrome, Crohn's disease, ileitis, ulcerative colitis, dysmenorrheal, cystitis, pancreatitis and pelvic pain). In another embodiment, the condition is pain resulting from musculo-skeletal disorders (including myalgia, fibromyalgia, spondylitis, seronegative (non-rheumatoid) arthropathies, non-articular rheumatism, dystrophinopathy, glycogenolysis, polymyositis and pyomyositis). In another embodiment, the condition is selected from the group consisting of heart and vascular pain (including pain caused by angina, myocardial infarction, mitral stenosis, pericarditis, Raynaud's phenomenon, scleredoma and skeletal muscle ischemia).

In another embodiment, the condition is selected from the group consisting of head pain (including migraine such as migraine with aura and migraine without aura), cluster headache, tension-type headache mixed headache and headache associated with vascular disorders; orofacial pain, including dental pain, otic pain, burning mouth syndrome and temporomandibular myofascial pain).

In another embodiment, the condition is a urologic condition selected from the group consisting of bladder outlet obstruction; incontinence and benign prostatic hyperplasia.

In another embodiment, the condition is an ophthalmic condition selected from retinal disease; macular degeneration and glaucoma.

In another embodiment, the condition is selected from the group consisting of tubulointerstitial disorders; anal fissure; baldness; cancerous cachexia; cerebral apoplexy; disorders of gut motility; enteromotility disorders; dysmenorrhoea (primary and secondary); glaucoma; macular degeneration; antiplatelet; haemorrhoids; incontinence; irritable bowel syndrome (IBS); tumor metastasis; multiple sclerosis; neoplasia; nitrate intolerance; nutcracker oesophagus; osteoporosis; infertility; premature labor; psoriasis; retinal disease; skin necrosis; and urticaria. In another embodiment, the condition is osteoporosis.

In another embodiment, the condition is associated with endothelial dysfunction, particularly conditions selected from the group consisting of atherosclerotic lesions, myocardial ischaemia, peripheral ischaemia, valvular insufficiency, pulmonary arterial hypertension, angina, vascular complications after vascular bypass, vascular dilation, vascular repermeabilisation, and heart transplantation.

The methods and compositions of the present invention are suitable for use with, for example, mammalian subjects such as humans, other primates (e.g., monkeys, chimpanzees), companion animals (e.g., dogs, cats, horses), farm animals (e.g., goats, sheep, pigs, cattle), laboratory animals (e.g., mice, rats), and wild and zoo animals (e.g., wolves, bears, deer). In another embodiment, the subject is a human.

I. USE IN THE PREPARATION OF A MEDICAMENT

The present invention further comprises methods for the preparation of a pharmaceutical composition (or "medicament") comprising Form A, Form B, Form C or combinations of such forms, in combination with one or more pharmaceutically-acceptable carriers and/or other active ingredients for use in treating the conditions described above.

J. WORKING EXAMPLES

Example 1

Preparation of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

Step 1

Dimethyl 1-(2-ethoxyethyl)-4-nitro-1H-pyrazole-3,5-dicarboxylate

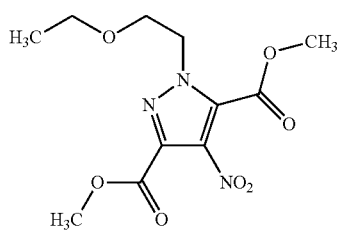 [SMILES: CCOCCn1nc(C(=O)OC)c([N+](=O)[O-])c1C(=O)OC]

Dimethyl 4-nitro-1H-pyrazole-3,5-dicarboxylate (2.0 g, 8.83 mmol, WO00/24745, page 48, preparation 2) was added to a solution of 2-ethoxyethyl bromide (1.18 mL, 10.45 mmol) and potassium carbonate (1.32 g, 9.56 mmol) in N,N-dimethylformamide (35 mL) and the reaction mixture stirred for 48 hours at room temperature. The reaction mixture was concentrated in vacuo and the residue partitioned between ethyl acetate (200 mL) and water (100 mL). The organic layer was separated, dried over magnesium sulphate and concentrated in vacuo. The crude product was purified by column chromatography on silica gel eluting with pentane:ethyl acetate 100:0 to 70:30 to yield the title product, 1.63 g.

$^1$H NMR (CDCl$_3$, 400 MHz) δ: 1.07 (s, 3H), 3.41 (q, 2H), 3.73 (t, 2H), 3.89 (s, 3H), 3.94 (s, 3H), 4.76 (t, 2H). MS APCI+ m/z 302, [MH]$^+$.

Step 2

4-Nitro-1-(2-ethoxyethyl)-1H-pyrazole-3,5-dicarboxylic acid 3-methyl ester

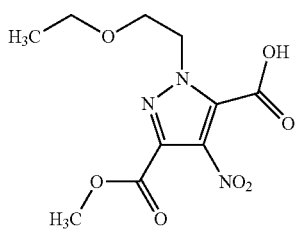 [SMILES: CCOCCn1nc(C(=O)OC)c([N+](=O)[O-])c1C(=O)O]

The ester of Step 1 (1.63 g, 5.4 mmol) was added to a solution of potassium hydroxide (330 mg, 5.9 mmol) in methanol (20 mL) and the reaction mixture stirred at room temperature for 18 hours. The reaction mixture was concentrated in vacuo and the crude product dissolved in water and washed with ether. The aqueous phase was acidified with 2M hydrochloric acid and extracted into dichloromethane (3×100 mL). The organics were combined, dried over magnesium sulphate and concentrated in vacuo to yield the title product.

$^1$H NMR (CD$_3$OD, 400 MHz) δ: 1.07 (s, 3H), 3.47 (q, 2H), 3.80 (t, 2H), 3.88 (s, 3H), 4.77 (t, 2H). MS APCI+ m/z 288 [MH]$^+$.

Step 3

Methyl 5-carbamoyl-1-(2-ethoxyethyl)-4-nitro-1H-pyrazole-3-carboxylate

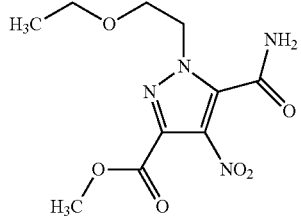

Oxalyl chloride (1.2 mL, 13.76 mmol) and N,N-dimethylformamide (39 µL) were added to a solution of the carboxylic acid of Step 2 (1.33 g, 4.63 mmol) in dichloromethane (20 mL) and the reaction mixture stirred at room temperature for 2 hours. The reaction mixture was concentrated in vacuo and azeotroped from dichloromethane (3×50 mL). The product was dissolved in tetrahydrofuran (50 mL), cooled in an ice bath, treated with 0.88 ammonia solution (10 mL) and stirred for 18 hours at room temperature. The mixture was concentrated in vacuo and the residue partitioned between dichloromethane (200 mL) and water (50 mL). The organics phase was dried over magnesium sulphate and concentrated in vacuo to yield the title product.

$^1$H NMR (DMSO-D$_6$, 400 MHz) δ: 1.06 (t, 3H), 3.40 (m, 2H), 3.77 (m, 2H), 3.84 (s, 3H), 4.38 (m, 2H), 8.35 (m, 1H), 8.46 (m, 1H). MS APCI+ m/z 287 [MH]$^+$.

Step 4

Methyl 4-amino-5-carbamoyl-1-(2-ethoxyethyl)-1H-pyrazole-3-carboxylate

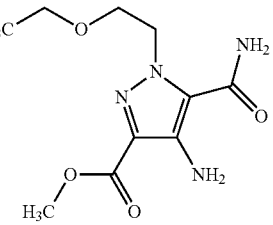

Palladium(II) hydroxide (100 mg) was added to a solution of the nitro compound of Step 3 (970 mg, 3.39 mmol) in methanol (20 mL) and the mixture warmed to reflux. Ammonium formate (1.07 g, 16.97 mmol) was added and the reaction mixture stirred at reflux for 2 hours. The catalyst was removed by filtration through Arbocel® and the reaction mixture concentrated in vacuo to yield the title product.

¹H NMR (DMSO-D₆, 400 MHz) δ: 1.02 (t, 3H), 3.33 (m, 2H), 3.66 (m, 2H), 3.80 (s, 3H), 4.57 (m, 2H), 5.11 (m, 2H), 7.49 (m, 2H), MS APCI+ m/z 257 [MH]⁺.

Step 5

Methyl 1-(2-ethoxyethyl)-5,7-dioxo-4,5,6,7-tetrahydro-1H-pyrazolo[4,3-d]pyrimidine-3-carboxylate

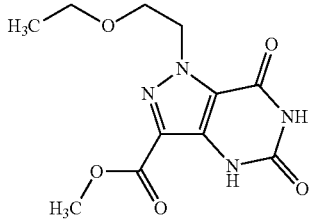 [SMILES: CCOCCn1nc(C(=O)OC)c2[nH]c(=O)[nH]c(=O)c21]

A solution of the amide of Step 4 (570 mg, 3.38 mmol) in N,N-dimethylformamide (30 mL) was treated with N,N'-carbonyldiimidazole (658 mg, 4.06 mmol) and the reaction mixture stirred at room temperature for 1 hour and then at 90° C. for 18 hours. The reaction mixture was concentrated in vacuo and the crude product suspended in acetone and sonicated for 30 minutes. The solid product was filtered off and dried in vacuo to yield the title product.

¹H NMR (DMSO-D₆, 400 MHz) δ: 1.02 (t, 3H), 3.37 (m, 2H), 3.77 (m, 2H), 3.83 (s, 3H), 4.63 (m, 2H), 10.75 (s, 1H), 11.40 (s, 1H). MS ES– m/z 281 [M-H]⁻.

Step 6

Methyl 5,7-dichloro-1-(2-ethoxyethyl)-1H-pyrazolo[4,3-d]pyrimidine-3-carboxylate

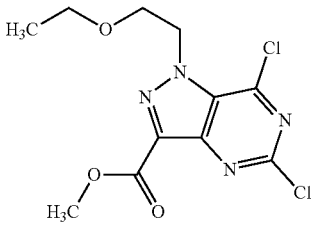 [SMILES: CCOCCn1nc(C(=O)OC)c2nc(Cl)nc(Cl)c21]

Phosphorous oxychloride (934 µL, 10.0 mmol) and tetraethylammonium chloride (195 mg, 1.50 mmol) were added to a solution of the dione of Step 5 (140 mg, 0.50 mmol) in propionitrile (5 mL) and the reaction mixture refluxed for 18 hours. The reaction mixture was concentrated in vacuo and the crude product partitioned between ethyl acetate (50 mL) and water (50 mL). The organic layer was dried over magnesium sulphate and concentrated in vacuo. The crude product was purified by column chromatography on silica gel eluting with pentane:ethyl acetate 100:0 to 75:25 to yield the title product.

¹H NMR (CDCl₃, 400 MHz) δ: 1.05 (t, 3H), 3.41 (m, 2H), 3.84 (m, 2H), 4.06 (s, 3H), 5.00 (m, 2H). MS APCI+ m/z 319 [MH]⁺.

Step 7

Methyl 5-chloro-1-(2-ethoxyethyl)-7-(4-methylpyridin-2-yl-amino)-1H-pyrazolo[4,3-d]pyrimidine-3-carboxylate

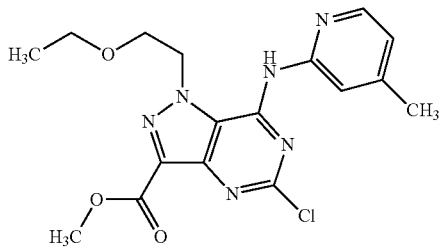

The dichloro compound of Step 6 (1.98 g, 6.20 mmol) was dissolved in dimethyl sulphoxide (10 mL) and the solution treated with 2-amino-4-methylpyridine (1.34 g, 12.4 mmol). The reaction mixture was stirred at room temperature for 18 hours. The reaction mixture was partitioned between dichloromethane (300 mL) and water (500 mL) and the dichloromethane layer separated. The organic phase was washed with water (3×100 mL), dried over magnesium sulphate and concentrated in vacuo. The residue was purified by column chromatography on silica gel eluting with dichloromethane:methanol 100:0 to 98:2. The crude product was triturated with ether (50 mL), filtered and concentrated in vacuo to yield the title product, 1.2 g.

¹H-NMR (CDCl₃, 400 MHz) δ: 1.06 (t, 3H), 2.49 (s, 3H), 3.62 (m, 2H), 4.00 (t, 2H), 4.06 (s, 3H), 5.05 (m, 2H), 6.98 (m, 1H), 8.16 (m, 1H), 8.50 (m, 1H). MS APCI+ m/z 391 [MH]⁺.

Step 8

5-Chloro-7-(4-methylpyridin-2-yl-amino)-1-(2-ethoxyethyl)-1H-pyrazolo[4,3-d]pyrimidine-3-carboxylic acid

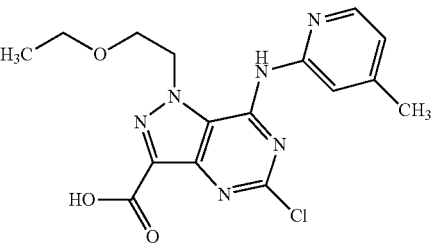 [SMILES: CCOCCn1nc(C(=O)O)c2nc(Cl)nc(Nc3cc(C)ccn3)c21]

The ester of Step 7 (4.3 g, 11 mmol) was dissolved in dioxan (50 mL) and the solution treated with a 1M aqueous solution of sodium hydroxide (22.0 mL, 22.0 mmol). The reaction mixture was then stirred for 18 hours at room temperature. The reaction mixture was evaporated to dryness, the residue dissolved in water (100 mL) and washed with dichloromethane (50 mL). The aqueous phase was then acidified with 1M citric acid solution to pH 4-5 and a yellow precipitate formed. The mixture was stirred for 15 minutes before being filtered and the solid product dried in vacuo over phosphorus pentoxide to yield the title product, 3.75 g.

¹H NMR (DMSO-D₆, 400 MHz) δ: 1.00 (t, 3H), 2.34 (s, 3H), 3.45 (m, 2H), 3.81 (m, 2H), 4.84 (m, 2H), 6.93 (m, 1H), 7.89 (m, 1H), 8.16 (m, 1H).

Step 9

N-[5-Chloro-1-(2-ethoxyethyl)-7-(4-methylpyridin-2-yl-amino)-1H-pyrazolo[4,3-d]pyrimidine-3-carbonyl]methanesulfonamide

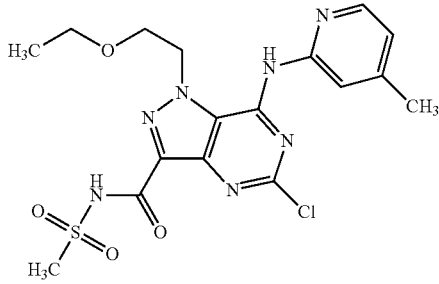 [SMILES: CCOCCn1nc(C(=O)NS(C)(=O)=O)c2nc(Cl)nc(Nc3cc(C)ccn3)c21]

The carboxylic acid of Step 8 (1.0 g, 2.70 mmol), methanesulphonamide (330 mg, 3.5 mmol), 1-(3-dimethylaminopropyl)-3-ethylcarbodiimide hydrochloride (660 mg, 3.5 mmol) and 4-dimethylaminopyridine (390 mg, 3.5 mmol) were dissolved in N,N-dimethylformamide (10 mL) and the reaction mixture stirred at room temperature for 60 hours. Additional methanesulphonamide (165 mg, 1.7 mmol), 1-(3-dimethylaminopropyl)-3-ethylcarbodiimide hydrochloride (330 mg, 1.7 mmol) and 4-dimethylaminopyridine (195 mg, 1.7 mmol) were added and the reaction mixture stirred for a further 20 hours. Further methanesulphonamide (165±1.7 mmol), 1-(3-dimethylaminopropyl)-3-ethylcarbodiimide hydrochloride (330 mg, 1.7 mmol) and 4-dimethylaminopyridine (195 mg 1.7 mmol) were added and the reaction mixture stirred for a final 18 hours. The reaction mixture was concentrated in vacuo and the residue partitioned between dichloromethane (25 mL) and water (25 mL). The organic phase was separated, washed with water (2×25 mL), dried over magnesium sulphate and concentrated in vacuo. The residue was purified by column chromatography on silica gel eluting with dichloromethane:methanol:acetic acid 100:0:0 to 96:3.5:0.5. The crude product was triturated in warm ethyl acetate (10 mL) to yield the title product, 290 mg.
¹H NMR (DMSO-D₆, 400 MHz) δ: 0.95 (t, 3H), 2.40 (s, 3H), 3.40 (s, 3H), 3.45 (d, 2H), 3.85 (m, 2H), 4.95 (m, 2H), 7.15 (d, 1H), 7.85 (s, 1H), 8.25 (d, 1H). MS ES– m/z 452 [M-H]⁻.

Step 10

N-[1-(2-Ethoxyethyl)-5-(N-ethyl-N-methylamino)-7-(4-methylpyridin-2-yl-amino)-1H-pyrazolo[4,3-d]pyrimidine-3-carbonyl]methanesulfonamide

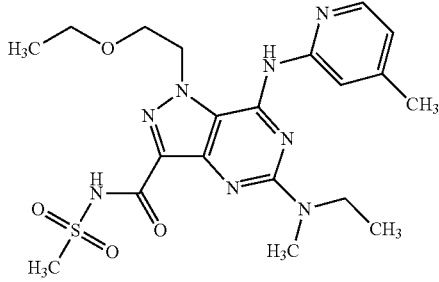 [SMILES: CCOCCn1nc(C(=O)NS(C)(=O)=O)c2nc(N(C)CC)nc(Nc3cc(C)ccn3)c21]

Figure 14:
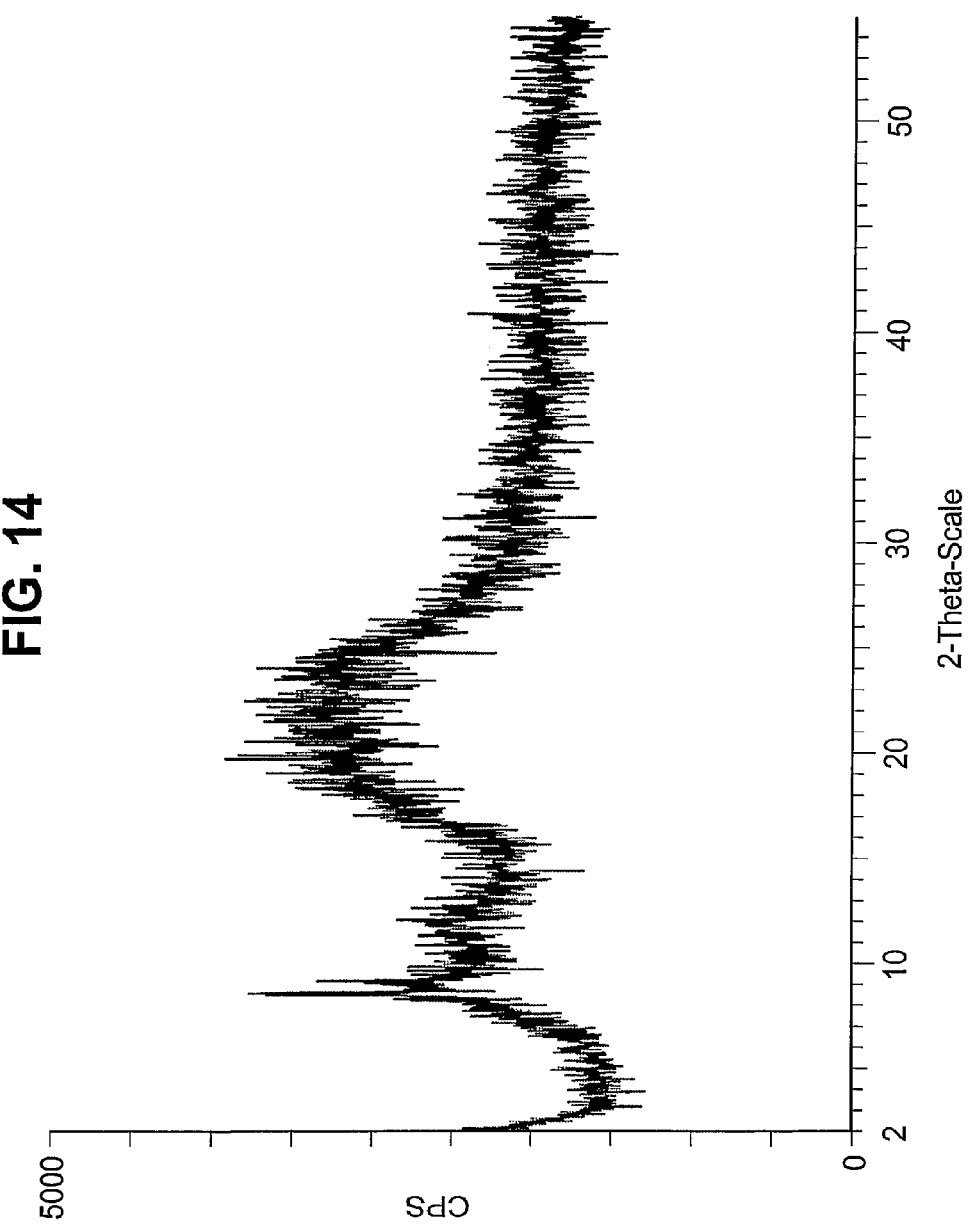
FIG. 14 shows an X-ray powder diffraction pattern for the material prepared in Example 1.

The chloro compound of Step 9 (110 mg, 0.24 mmol), N-methyl-ethylamine (79 mg, 1.2 mmol), N-ethyldiisopropylamine (210 µL, 1.20 mmol) and caesium fluoride (37 mg, 0.24 mmol) were dissolved in dimethyl sulphoxide (1 mL) and the reaction mixture heated to 110° C. for 5 hours in a ReactiVial™. The reaction mixture was partitioned between ethyl acetate (10 mL) and water (10 mL) and the organic phase separated and washed with water (2×10 mL). The organic phase was then dried over magnesium sulphate and concentrated in vacuo. The residue was purified by column chromatography on silica gel eluting with dichloromethane:methanol 99:1 to 97:3. The purified material was evaporated and dried to yield a pale yellow solid (66 mg). The PXRD pattern for the solid is shown as FIG. 14.
¹H NMR (DMSO-D₆+CF₃CO₂D, 400 MHz) δ: 0.99 (t, 3H), 1.17 (t, 3H), 2.44 (s, 3H), 3.18 (s, 3H), 3.41 (s, 3H), 3.44 (d, 2H), 3.66 (d, 2H), 3.88 (t, 2H), 4.93 (t, 2H), 7.16 (d, 1H), 8.09 (s, 1H), 8.26 (d, 1H). MS ES– m/z 475 [M-H]⁻.

Example 2

Figure 15:
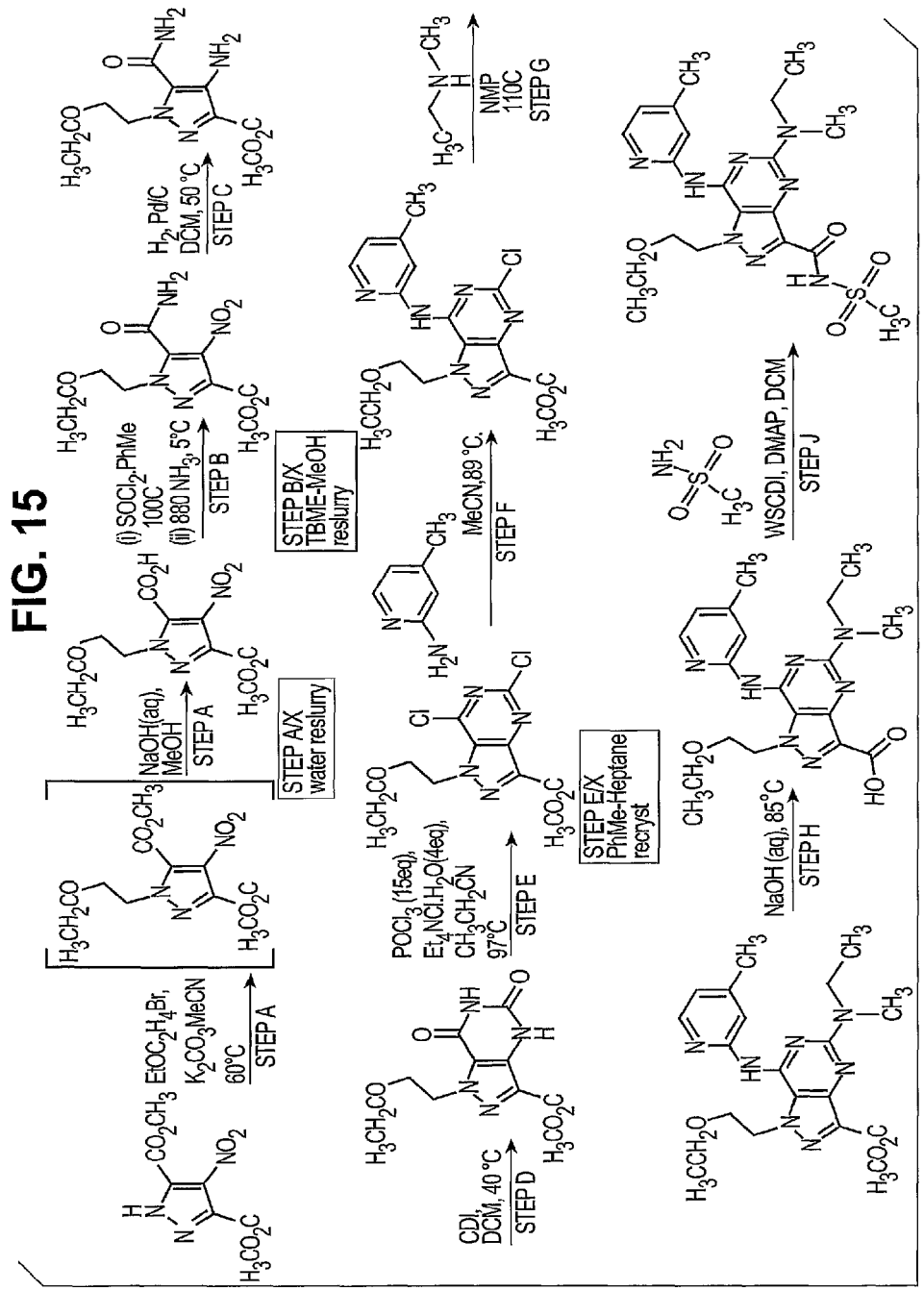
FIG. 15 shows an illustrative alternative synthetic scheme for the preparation of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Preparation of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide An alternative synthetic scheme for the preparation of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide is described in the synthetic scheme shown as FIG. 15.

Example 3

Preparation of Form A (Recrystallization From Ethyl Acetate)

Form A crystalline N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

Step 1

Dimethyl 1-(2-ethoxyethyl)-4-nitro-1H-pyrazole-3,5-dicarboxylate

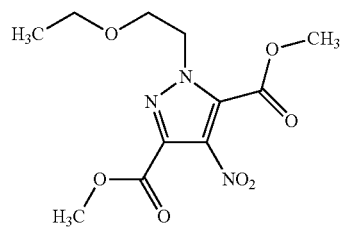

Dimethyl 4-nitro-1H-pyrazole-3,5-dicarboxylate (WO00/24745, page 48, preparation 2) (2.0 g, 8.83 mmol) was added to a solution of 2-ethoxyethyl bromide (1.18 mL, 10.45 mmol) and potassium carbonate (1.32 g, 9.56 mmol) in N,N-dimethylformamide (35 mL) and the reaction mixture stirred for 48 hours at room temperature. The reaction mixture was concentrated in vacuo and the residue partitioned between ethyl acetate (200 mL) and water (100 mL). The organic layer was separated, dried over magnesium sulphate and concentrated in vacuo. The crude product was purified by column chromatography on silica gel eluting with pentane: ethyl acetate 100:0 to 70:30 to yield the ester product, 1.63 g.

¹H NMR (CDCl₃, 400 MHz) δ: 1.07 (s, 3H), 3.41 (q, 2H), 3.73 (t, 2H), 3.89 (s, 3H), 3.94 (s, 3H), 4.76 (t, 2H). MS APCI+ m/z 302, [MH]⁺.

Step 2

4-Nitro-1-(2-ethoxyethyl)-1H-pyrazole-3,5-dicarboxylic acid 3-methyl ester

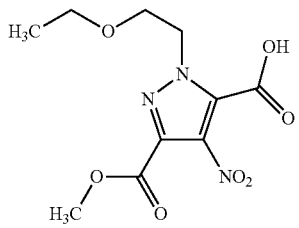 [SMILES: CCOCCn1nc(C(=O)OC)c([N+](=O)[O-])c1C(=O)O]

The ester of step 1 (1.63 g, 5.4 mmol) was added to a solution of potassium hydroxide (330 mg, 5.9 mmol) in methanol (20 mL) and the reaction mixture stirred at room temperature for 18 hours. The reaction mixture was concentrated in vacuo and the crude product dissolved in water and washed with ether. The aqueous phase was acidified with 2M hydrochloric acid and extracted into dichloromethane (3×100 mL). The organics were combined, dried over magnesium sulphate and concentrated in vacuo to yield the nitro product.

¹H NMR (CD₃OD, 400 MHz) δ: 1.07 (s, 3H), 3.47 (q, 2H), 3.80 (t, 2H), 3.88 (s, 3H), 4.77 (t, 2H). MS APCI+ m/z 288 [MH]⁺.

Step 3

Methyl 5-carbamoyl-1-(2-ethoxyethyl)-4-nitro-1H-pyrazole-3-carboxylate

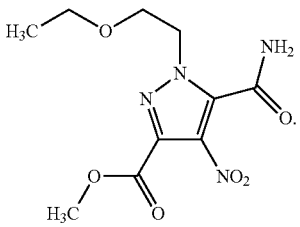

Oxalyl chloride (1.2 mL, 13.76 mmol) and N,N-dimethylformamide (39 μL) were added to a solution of the carboxylic acid of step 2 (1.33 g, 4.63 mmol) in dichloromethane (20 mL) and the reaction mixture stirred at room temperature for 2 hours. The reaction mixture was concentrated in vacuo and azeotroped from dichloromethane (3×50 mL). The product was dissolved in tetrahydrofuran (50 mL), cooled in an ice bath, treated with 0.88 ammonia solution (10 mL) and stirred for 18 hours at room temperature. The mixture was concentrated in vacuo and the residue partitioned between dichloromethane (200 mL) and water (50 mL). The organics phase was dried over magnesium sulphate and concentrated in vacuo to yield the nitro product. ¹H NMR (DMSO-D₆, 400 MHz) δ: 1.06 (t, 3H), 3.40 (m, 2H), 3.77 (m, 2H), 3.84 (s, 3H), 4.38 (m, 2H), 8.35 (m, 1H), 8.46 (m, 1H). MS APCI+ m/z 287 [MH]⁺.

Step 4

Methyl 4-amino-5-carbamoyl-1-(2-ethoxyethyl)-1H-pyrazole-3-carboxylate

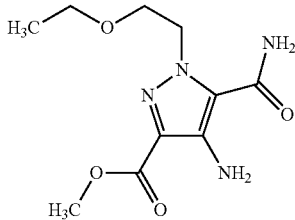

Palladium (II) hydroxide (100 mg) was added to a solution of the nitro compound of step 3 (970 mg, 3.39 mmol) in methanol (20 mL) and the mixture warmed to reflux. Ammonium formate (1.07 g, 16.97 mmol) was added and the reaction mixture stirred at reflux for 2 hours. The catalyst was removed by filtration through Arbocel® and the reaction mixture concentrated in vacuo to yield the amide product.

¹H NMR (DMSO-D₆, 400 MHz) δ: 1.02 (t, 3H), 3.33 (m, 2H), 3.66 (m, 2H), 3.80 (s, 3H), 4.57 (m, 2H), 5.11 (m, 2H), 7.49 (m, 2H). MS APCI+ m/z 257 [MH]⁺.

Step 5

Methyl 1-(2-ethoxyethyl)-5,7-dioxo-4,5,6,7-tetrahydro-1H-pyrazolo[4,3-d]pyrimidine-3-carboxylate

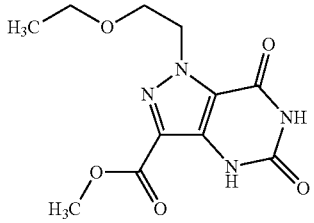 [SMILES: CCOCCn1nc(C(=O)OC)c2[nH]c(=O)[nH]c(=O)c21]

A solution of the amide of step 4 (570 mg, 3.38 mmol) in N,N-dimethylformamide (30 mL) was treated with N,N'-carbonyldiimidazole (658 mg, 4.06 mmol) and the reaction mixture stirred at room temperature for 1 hour and then at 90° C. for 18 hours. The reaction mixture was concentrated in vacuo and the crude product suspended in acetone and sonicated for 30 minutes. The solid product was filtered off and dried in vacuo to yield the dione product. ¹H NMR (DMSO-D₆, 400

MHz) δ: 1.02 (t, 3H), 3.37 (m, 2H), 3.77 (m, 2H), 3.83 (s, 3H), 4.63 (m, 2H), 10.75 (s, 1H), 11.40 (s, 1H). MS ES– m/z 281 [M-H]⁻.

Step 6

Methyl 5,7-dichloro-1-(2-ethoxyethyl)-1H-pyrazolo[4,3-d]pyrimidine-3-carboxylate

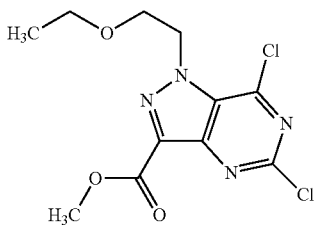 [SMILES: CCOCCn1nc(C(=O)OC)c2nc(Cl)nc(Cl)c21]

Phosphorous oxychloride (934 μL, 10.0 mmol) and tetraethylammonium chloride (195 mg, 1.50 mmol) were added to a solution of the dione of step 5 (140 mg, 0.50 mmol) in propionitrile (5 mL) and the reaction mixture refluxed for 18 hours. The reaction mixture was concentrated in vacuo and the crude product partitioned between ethyl acetate (50 mL) and water (50 mL). The organic layer was dried over magnesium sulphate and concentrated in vacuo. The crude product was purified by column chromatography on silica gel eluting with pentane:ethyl acetate 100:0 to 75:25 to yield the dichloro product.
¹H NMR (CDCl₃, 400 MHz) δ: 1.05 (t, 3H), 3.41 (m, 2H), 3.84 (m, 2H), 4.06 (s, 3H), 5.00 (m, 2H). MS APCI+ m/z 319 [MH]⁺.

Step 7

Methyl 5-chloro-1-(2-ethoxyethyl)-7-(4-methylpyridin-2-yl-amino)-1H-pyrazolo[4,3-d]pyrimidine-3-carboxylate

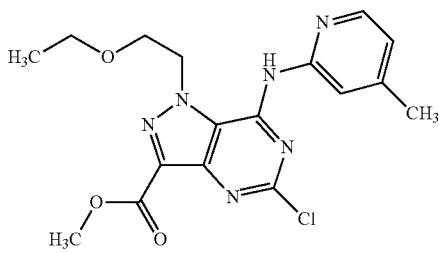 [SMILES: CCOCCn1nc(C(=O)OC)c2nc(Cl)nc(Nc3cc(C)ccn3)c21]

The dichloro compound of step 6 (1.98 g, 6.20 mmol) was dissolved in dimethyl sulphoxide (10 mL) and the solution treated with 2-amino-4-methylpyridine (1.34 g, 12.4 mmol). The reaction mixture was stirred at room temperature for 18 hours. The reaction mixture was partitioned between dichloromethane (300 mL) and water (500 mL) and the dichloromethane layer separated. The organic phase was washed with water (3×100 mL), dried over magnesium sulphate and concentrated in vacuo. The residue was purified by column chromatography on silica gel eluting with dichloromethane:methanol 100:0 to 98:2. The crude product was triturated with ether (50 mL), filtered and concentrated in vacuo to yield the monochloro product, 1.2 g. ¹H-NMR (CDCl₃, 400 MHz) δ: 1.06 (t, 3H), 2.49 (s, 3H), 3.62 (m, 2H), 4.00 (t, 2H), 4.06 (s, 3H), 5.05 (m, 2H), 6.98 (m, 1H), 8.16 (m, 1H), 8.50 (m, 1H). MS APCI+ m/z 391 [MH]⁺.

Step 8

Methyl 1-(2-ethoxyethyl)-5-(N-ethyl-N-methylamino)-7-(6-ethylpyridin-2-ylamino)-1H-pyrazolo[4,3-d]pyrimidine-3-carboxylate

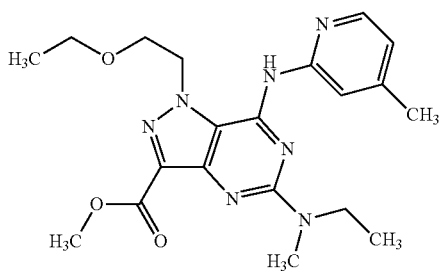 [SMILES: CCOCCn1nc(C(=O)OC)c2nc(N(C)CC)nc(Nc3cc(C)ccn3)c21]

A solution of N-ethylmethylamine (4.6 mL, 53.8 mmol) in N-methylpyrrolidin-2-one (7 mL) was added to a solution of the monochloro compound of step 7 (7.0 g, 17.93 mmol) in N-methylpyrrolidin-2-one (28 mL) at 110 C. The reaction mixture was heated overnight and on completion the solution was cooled to room temperature and water (25 mL) was added. After stirring at room temperature for 2 hours the slurry was filtered and washed with 2×15 mL water. The solid was dried overnight in vacuo at 55 C to give an orange solid (5.988 g, 15.0 mmol, 84%).
¹H NMR (CD₃OD, 400 MHz) δ: 1.12 (m, 3H), 1.25 (m, 3H), 2.40 (s, 3H), 3.21 (m, 2H), 3.23 (s, 3H), 3.60 (m, 2H), 3.75 (m, 2H), 3.96 (s, 3H), 4.80 (m, 2H), 6.94 (m, 1H), 8.16 (m, 1H), 8.34 (m, 1H). MS APCI– m/z 412 [M-H]⁻.

Step 9

1-(2-Ethoxyethyl)-5-(N-ethyl-N-methylamino)-7-(6-ethylpyridin-2-ylamino)-1H-pyrazolo[4,3-d]pyrimidine-3-carboxylic Acid

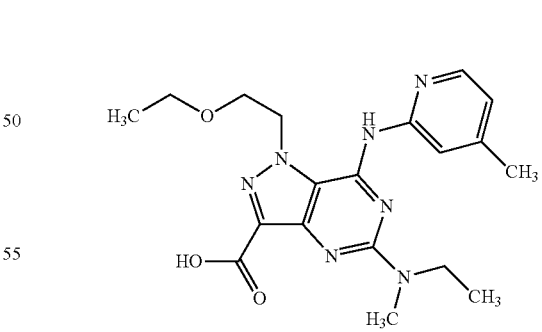

The ester of step 8 (13.57 g, 32.83 mmol) and a 1M aqueous solution of sodium hydroxide (90 mL) were dissolved in methanol (10 mL) and the reaction mixture stirred at 85 C for 1 hour. The reaction mixture was cooled to room temperature and acidified with 10% aqueous citric acid (90 mL). The aqueous layer was extracted twice with dichloromethane (36 mL and 24 mL). The aqueous layer was further acidified with 10% aqueous citric acid (20 mL) and extracted with dichloromethane (24 mL). The combined dichloromethane extracts were combined and ethanol (13 mL) was added. The solution was distilled at ambient pressure and the distilled dichloromethane replaced with ethanol (52 mL). Water (12 mL) was added and the mixture was cooled to 5 C and stirred for 1 hour. The slurry was filtered and washed with water (24 mL) and dried in vacuo at 55 C to give a yellow solid (8.858 g, 22.2 mmol, 68%)

$^1$H NMR (CD$_3$OD, 400 MHz) δ: 1.10 (t, 3H), 1.30 (t, 3H), 2.43 (s, 3H), 3.24 (s, 3H), 3.57 (m, 2H), 3.70 (m, 2H), 3.93 (t, 2H), 4.84 (m, 2H), 7.02 (m, 1H), 8.13 (m, 1H), 8.16 (m, 1H). MS APCI+ m/z 400 [M-H]$^+$.

Step 10

N-[1-(2-Ethoxyethyl)-5-(N-ethyl-N-methylamino)-7-(4-methylpyridin-2-ylamino)-1H-pyrazolo[4,3-d]pyrimidine-3-carbonyl]methanesulfonamide

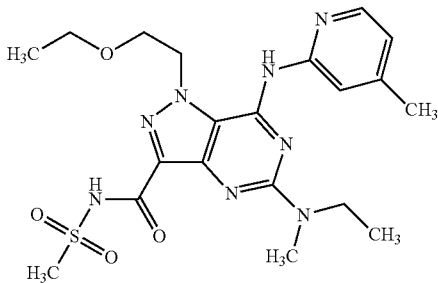

The carboxylic acid of step 9 (29.0 g, 72.6 mmol), methanesulphonamide (8.28 g, 87 mmol), 1-(3-dimethylaminopropyl)-3-ethylcarbodiimide hydrochloride (18.0 g, 94 mmol) and 4-dimethylaminopyridine (10.59 g, 94 mmol) were dissolved in dichloromethane (385 mL) and the reaction mixture stirred at room temperature overnight. The reaction mixture was diluted with dichloromethane (to 1500 mL) and washed twice with aqueous citric acid (50 g in 200 mL), then washed once with an acidic solution of a mixture of citric acid and sodium hydroxide. The dichloromethane phase was dried over magnesium sulphate and concentrated in vacuo. The solid residue was refluxed in isopropanol (1 L) for 20 minutes, allowed to cool and the resulting solid filtered off. The isolated yellow solid was then refluxed in ethyl acetate (2000 mL) until solution occurred, whereupon the volume of ethyl acetate was reduced to 1000 mL. The resulting solution was filtered and allowed to cool to room temperature overnight and then placed in an ice bath and stirred for 1.5 hours. The resulting solid was filtered off and washed with ether (2×50 ml), dried on the filter pad for 3 hours and then in vacuo over phosphorus pentoxide to yield a white powder (16.7 g). PXRD analysis of the powder indicated that it was the Form A crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

$^1$H NMR (CDCl$_3$, 400 MHz) δ: 1.20 (t, 3H), 1.29 (t, 3H), 2.41 (s, 3H), 3.24 (s, 3H), 3.45 (s, 3H), 3.64 (q, 2H), 3.75 (m, 2H), 3.99 (t, 2H), 4.82 (m, 2H), 6.87 (d, 1H), 8.20 (d, 1H), 8.29 (s, 1H), 9.87 (br, 1H). MS ES+ m/z 477 [MH]$^+$. Found C, 50.25: H, 5.90: N, 23.41: Calculated for C20H28N8O4S; C, 50.41: H, 5.92: N, 23.51.

Example 4

Preparation of Form A (Recrystallization from Isopropyl Alcohol)

The Form A crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

N-[1-(2-Ethoxyethyl)-5-(N-ethyl-N-methylamino)-7-(4-methylpyridin-2-ylamino)-1H-pyrazolo[4,3-d]pyrimidine-3-carbonyl]methanesulfonamide

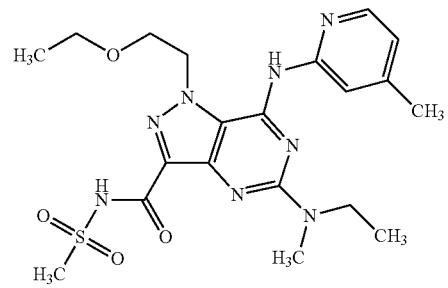

Crude N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide (16.7 g) (see Example 1) was slurried in dichloromethane (20 mL) and isopropyl alcohol (70 mL). The slurry was heated to reflux (about 60° C.) and the solid material appeared to remain substantially undissolved. An additional amount of dichloromethane (40 mL) was added in 5 mL increments to the slurry. The resulting solution was refluxed for about one minute and heating was stopped. At the end of this time the solid appeared to have dissolved to yield a yellow solution. The solution was then cooled to 35° C. with no sign of crystallization. The solution was seeded with a small amount (less than about 0.5 g) of crude N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide with no sign of crystallization. The solution was further cooled to room temperature with no sign of crystallization. When cooled to 5° C., the solution became a slurry. This slurry was stirred at a similar temperature, then filtered and the material collected on the filter was dried at 50° C. to yield a solid (7.7 g). PXRD analysis of the solid indicated that it was the Form A crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 5

Preparation of Form B (Methanol Reflux)

The Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

N-[1-(2-Ethoxyethyl)-5-(N-ethyl-N-methylamino)-7-(4-methylpyridin-2-ylamino)-1H-pyrazolo[4,3-d]pyrimidine-3-carbonyl]methanesulfonamide (13.9 g) containing crystalline form Form A (see Example 3) was dissolved in refluxing dichloromethane (160 mL) and methanol (200 mL). Dichloromethane was distilled out (approximately 110 mL distillate collected). The mixture was cooled to room temperature, granulated for 30 minutes, and filtered. The solids were washed with methanol (30 mL), and dried in vacuo to yield a bright yellow solid (10.8 g). PXRD analysis of the solid indicated that it was the Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 6

Preparation of Form B (Methanol Reflux)

The Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:
1-(2-Ethoxyethyl)-5-(N-ethyl-N-methylamino)-7-(4-methylpyridin-2-ylamino)-1H-pyrazolo[4,3-d]pyrimidine-3-carboxylic acid (1.19 kg, 2.98 mole) (see Example 3, Step 9), methanesulphonamide (344 g, 3.6 mole), 1-(3-dimethylaminopropyl)-3-ethylcarbodiimide hydrochloride (810.0 g, 4.21 mole), and 4-dimethylaminopyridine (488.8 g, 4.01 mole) were dissolved in dichloromethane (12 L) under a nitrogen atmosphere and the reaction mixture stirred at room temperature. After 3 hours, to the solution was added a further portion of 4-dimethylaminopyridine (62.0 g, total 551.7 g, 4.52 mole) and the reaction mixture stirred at room temperature for a further 20 hours. The reaction mixture was diluted with 10% aqueous citric acid (12 L) and the organic phase was separated, washed with 10% aqueous citric acid (12 L), and then washed with water.

The resulting solution (10 L) was filtered and was distilled at atmospheric pressure to approximately half of its initial volume, and the hot solution was diluted with portions of methanol (total 14 L) whilst dichloromethane was removed in portions by distillation (distillate fractions totaling 11 L, giving a final volume of 13 L which refluxes at 55° C.). The yellow slurry was cooled to room temperature, stirred overnight, and then cooled to 5° C. The slurry was then filtered and washed with chilled methanol portions (totaling 5.8 L). The material collected from the filter was dried in vacuum at 55° C. for 3 days to give the product as a bright yellow solid (1.038 kg, 73% yield) that it was the Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 7

Preparation of Form B (Dexoygenation and Methanol Reflux)

The Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:
Dichloromethane (260 mL) was refluxed with a flow of nitrogen through the vessel headspace, reducing the volume to 240 mL, and then cooled to room temperature under a nitrogen atmosphere. 1-(2-Ethoxyethyl)-5-(N-ethyl-N-methylamino)-7-(6-ethylpyridin-2-ylamino)-1H-pyrazolo[4,3-d]pyrimidine-3-carboxylic acid (24 g, 60 mmole) (see Example 3, Step 9), methanesulphonamide (6.88 g, 72 mmole), and 4-dimethylaminopyridine (10.98 g, 90 mmole) were dissolved in the dichloromethane (240 mL) under a nitrogen atmosphere. The solution was stirred for 30 minutes then 1-(3-dimethylaminopropyl)-3-ethylcarbodiimide hydrochloride (16.13 g, 84 mmole) was added and the reaction mixture was stirred at room temperature overnight under a nitrogen atmosphere. The reaction mixture was diluted with 10% aqueous citric acid (240 mL) and the organic phase was separated, washed with 10% aqueous citric acid (240 mL), and then washed with water (240 mL).

The resulting solution was distilled at atmospheric pressure to approximately half of its initial volume (approximately 120 mL). The hot solution was slowly diluted with methanol (240 mL) and then the mixture was distilled at atmospheric pressure to approximately 240 mL. The hot mixture was again diluted with methanol (120 mL), and again distilled at atmospheric pressure to approximately 240 mL. The hot mixture was yet again diluted with methanol (120 mL), and yet again distilled at atmospheric pressure to approximately 240 mL. The mixture was allowed to cool to room temperature with stirring over one hour, and then cooled and stirred at 0-5° C. for 1 hour. The resulting yellow slurry was then filtered and the solids washed with chilled methanol (96 mL). The solids were dried in vacuum overnight at 55° C. to give a bright yellow solid (25.78 g, 90% yield) that it was the Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 8

Preparation of Form B (Ion Exchange Resin and Methanol Reflux)

The Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:
1-(2-Ethoxyethyl)-5-(N-ethyl-N-methylamino)-7-(6-ethylpyridin-2-ylamino)-1H-pyrazolo[4,3-d]pyrimidine-3-carboxylic acid (24 g, 60.1 mmole) (see Example 3, Step 9), methanesulphonamide (6.88 g, 72.4 mmole), and 4-dimethylaminopyridine (10.98 g, 90 mmole) were dissolved in dichloromethane (240 mL) under a nitrogen atmosphere. The solution was stirred for 30 minutes then 1-(3-dimethylaminopropyl)-3-ethylcarbodiimide hydrochloride (16.14 g, 84.1 mmole) was added and the reaction mixture was stirred at room temperature until the reaction was judged essentially complete after 5 hours. The reaction mixture was diluted with 10% aqueous citric acid (240 mL) and the organic phase was separated, washed with 10% aqueous citric acid (240 mL), and then washed with water (240 mL).

To the stirred separated organic phase was added Amberlite IRN-78 (24 g) (a basic ion-exchange resin) and the mixture was stirred for 3 hours. The resin beads were filtered of, the filter cake was washed with dichloromethane (48 mL), and the combined filtrates were washed with 10% aqueous citric acid (120 mL), and then twice washed with water (240 mL).

The resulting solution was distilled at atmospheric pressure to approximately half of its initial volume (approximately 120 mL). The hot solution was slowly diluted with methanol (240 mL), precipitating a yellow solid, and then the mixture was distilled at atmospheric pressure to approximately 240 mL. The hot mixture was again diluted with methanol (240 mL), and again distilled at atmospheric pressure to approximately 240 mL. The yellow slurry was allowed to cool to room temperature with stirring overnight, and then cooled in an ice bath for 1 hour (to approximately 0-5° C.).

The resulting slurry was then filtered and the solids washed with methanol (96 mL). The solids were dried in vacuum overnight at 50° C. to give a bright yellow solid (21.51 g, 75.1% yield) that it was the Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 9

Preparation of Form B (Slurry Conversion)

Approximately 25 mg of Form A (see Example 3) was slurried at room temperature with 1 ml of methanol. There was a rapid increase in the yellow color of the slurry within 10 minutes. A small sample was removed from the slurry. PXRD analysis of the sample indicates that it was the Form B crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide.

Example 10

Preparation of Form B (Temperature Conversion)

A sample of Form A (see Example 3) was heated to 180° C. using DSC. The sample melts and recrystallizes as Form B. The sample was allowed to cool to room temperature. To confirm that no Form A remained and that the conversion to Form B was complete, the sample was heated again in the DSC to 175° C. No significant thermal events were detected. The sample was allowed to cool to room temperature. The sample was heated again to 250° C. The melt of form B was observed at 220° C.

Example 11

Preparation of Form C (Slurry Conversion)

The Form C crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

A sample of Form B (see Examples 5 to 9) was slurried in THF/H$_2$O (50:50 volume/volume) at 4° C. After 16 days a small sample was filtered and dried at room temperature, resulting in a light yellow solid. DSC analysis of the sample was consistent with Form C. Another small sample was removed in the wet state from the slurry. PXRD analysis of the sample was consistent with Form C. After 31 days of slurrying, another small sample was removed in the wet state from the slurry. PXRD analysis of the sample was consistent with Form C.

Example 12

Preparation of Form C (Seeding)

The Form C crystalline form of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide was prepared as follows:

A sample of Form B (see Examples 5 to 9) (129.6 g) was stirred in acetone (1300 ml) at 23° C. under an atmosphere of nitrogen. A seed of Form C (20 mg) was added, and stirring was continued for 13 days at ambient temperature. The solids were collected by filtration, and dried under vacuum at ambient temperature but above 20° C., to provide a 92.4% yield of the product Form C (119.8 g), displaying the powder X-ray diffraction pattern in FIG. 4.

Example 13

Stability of Form A and Form B

The thermodynamically stabilities of Form A and Form B were compared as described below. First, approximately 25 mg of Form A was slurried in approximately 1 ml of methanol. There was a rapid increase in the yellow color of the slurry. A small sample was removed from the slurry. PXRD analysis confirmed that the sample was Form B. Second, Form A and Form B were analyzed by DSC and illustrative data for samples of Form A and Form B are shown in FIGS. 5 and 6, respectively. The DSC data indicated that the melting point of Form B was higher than that of Form A. Accordingly, the results of both the slurry conversion analysis and the DSC analysis confirm that Form B is more thermodynamically stable than Form A.

Example 14

Stability of Form B and Form C

Bridging studies were performed in the following solvent systems to determine the relative thermodynamic stabilities of Form B and Form C: (1) THF/H$_2$O (50:50 volume/volume), (2) methyl ethyl ketone ("MEK"), (3) methanol, and (4) methanol/dichloromethane (DCM) (50:50 volume/volume). The MEK study was performed at room temperature while the studies with the other three solvent systems were performed at both 40° C. and 60° C. In each study a suspension of Form B in the appropriate solvent system was prepared. Approximately 10 mg of Form C was then added to each suspension. The suspensions were then allowed to slurry at the appropriate temperature for a specific period of time. The solvent system, temperature of the solvent system, and period of time over which the suspension was allowed to slurry are set forth below for each study:

(1) Study A: Slurried for 3 days in MEK at room temperature;
(2) Study B: Slurried for 3 days in THF/H$_2$O (50:50) at 40° C.;
(3) Study C: Slurried for 3 days in THF/H$_2$O (50:50) at 60° C.;
(4) Study D: Slurried for 21 days in Methanol at 40° C.;
(5) Study E: Slurried for 21 days in Methanol at 60° C.;
(6) Study F: Slurried for 5 days in Methanol/DCM at 40° C.; and
(7) Study G: Slurried for 21 days in Methanol/DCM at 60° C.

At the end of the specified time period, a sample was removed from each slurry and analyzed by PXRD. The PXRD analyses indicated that all of the samples produced at room temperature and at 40° C. were Form C and all of the samples produced at 60° C. were Form B. As discussed previously, there is a crossover in the thermodynamic stability of Form B and Form C at a temperature between 40 and 60° C. (i.e. the two forms are enantiotropes). At temperatures below this crossover point, Form C is the most thermodynamically stable form. At temperatures above this crossover point, Form B is the most thermodynamically stable form.

Example 15

Ex Vivo Assays

Method A: Aortic Ring Assay

This protocol describes a procedure for measuring the direct relaxation of rat aortic rings exposed to N-[1-(2-ethoxyethyl)-5-(N-ethyl-N-methylamino)-7-(4-methylpyridin-2-yl-amino)-1H-pyrazolo[4,3-d]pyrimidine-3-carbonyl]

methanesulfonamide. In this assay, PDE5 inhibiting compounds elicit a relaxation of aortic rings by enhancing the cGMP signal evoked by a stable exogenous NO-donor, Diethyltriamine NONOate (diazen-1-ium-1,2-diolate) ("DETA-NO"). An $EC_{50}$, with 95% confidence intervals, for compound-evoked relaxation is calculated as an index of potency. The $EC_{50}$ is the concentration of the PDE5 inhibiting compound which produces 50% of the maximum possible effective response for the PDE5 inhibiting compound.

Male Sprague-Dawley rats (250-350 g) are asphyxiated by $CO_2$ gas and their thoracic aorta carefully excised and placed in Krebs buffer. The aortas are then carefully dissected free of connective tissue and divided into 8 sections, each 3-4 mm in length.

Aortic rings are suspended between parallel stainless steel wires in a water jacketed (37° C.), 15 mL tissue bath under a resting tension of 1 gram. Tension is measured using isometric tension transducers and recorded using Ponemah tissue platform system. Each preparation is allowed to equilibrate for at least 60 minutes prior to drug testing. During this time, the tissues are also incubated with 200 uM NG-monomethyl L-arginine ("L-NMMA"), and the incubation media changed every 15-20 minutes (L-NMMA is added after each wash to maintain the final concentration at 200 uM in each tissue bath).

Following the equilibration period, baseline tensions are recorded for each tissue. The vasoconstrictor response to phenylepherine (1 uM) is assessed and when the response to phenylepherine reached a maximum, vascular reactivity was subsequently assessed by a challenge of acetylcholine (1 uM). Following another washout period, a second baseline value is recorded, the vasoconstrictor noradrenaline (25 nM) is added to each bath and the tissues incubated for a time period (about 15 minutes) sufficient for the tissues to achieve a stable tone. An exogenous NO drive is supplied using the stable NO-donor, DETA-NO. The concentration of DETA-NO is titrated (cumulatively in half-log increments) to achieve approximately 5-15% relaxation of the noradrenaline-evoked preconstriction. Cumulative concentration-response curves are constructed in a single ring, typically using 5 doses/ring and allowing 15 minutes between each addition.

Method B: Aortic Ring Assay

The protocol of Method A can be modified to provide an alternative protocol to measure the relaxation of rat aortic rings exposed to PDE5 inhibiting compounds. This alternative method varies from Method A as described below:

For the alternative method, the endothelium is first removed by gently rubbing the lumen of the vessel together between the fingers prior to preparing the rings (denuded rings). The resting tension is set at 2 grams and the vasoconstrictor response to a maximal concentration of phenylepherine (1 μM) is assessed, followed (after a washout period) by two further exposures to 300 nM of pheylephrine. The concentration-response relationship to noradrenaline is constructed in each tissue over concentration range 0.1 to 300 nM. After another washout period, the tissues are constricted with an $EC_{90}$ concentration of noradrenaline for compound testing.

Example 16

In Vivo Assays

Method A: Culex™ Assay

A conscious pre-cannulated spontaneously hypertensive rat (SHR) model is used for evaluating the efficacy of N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide in lowering systemic arterial blood pressure. This assay is conducted using an automated blood sampler ("ABS") system. The Culex™ ABS system (Bioanalytical System, Inc., West Lafayette, Ind.) comprises a laptop computer, four control units and metabolic cages. This ABS system allows for the collection of multiple blood samples from a single rat without causing undue stress to the animal.

In addition, the ABS system allows for the collection of urine samples that can be potentially used for biomarker identifications. Through this approach, efficacy and standard pharmacokinetic studies are conducted in the conscious unrestrained SHR rats simultaneously to define the relationship between plasma free drug concentration or potential biomarker(s) and pharmacological effect (reduction of mean arterial blood pressure).

SHR rats at 12 to 16 weeks of age, weighing about 300 g, undergo surgical cannulation of both jugular veins and the right carotid artery. After surgical recovery, animals are placed in the Culex™ cages and tethered to a movement-responsive arm with a sensor that controls cage movement when the animal moves to prevent the catheters from being twisted. Connections are made between the right jugular catheter and the Culex™ sterile tubing set for blood sampling, and the left jugular catheter for compound administration, and the catheter in the right carotid artery is connected to a pressure transducer for monitoring blood pressure. To keep the patency of the catheters, the right jugular cannula is maintained by the "tend" function of the Culex™ that flushes the catheter with 20 μL heparin saline (10 units/mL) every 12 minutes or between sampling events, and the left jugular cannula is filled with heparin saline (20 units/mL). The patency of the right carotid cannula is maintained by slow infusion of heparin saline either directly into the extend tubing when blood pressure is not recorded or through the pressure transducer during the blood pressure monitoring. Animals are allowed to acclimate for at least two hours before compound evaluation. The PDE5 inhibiting compounds may be administered intravenously or by oral gavage. Blood sampling protocols (sampling time and volume) are programmed using the Culex™ software. The total amount of blood withdrawn from each animal will not exceed 750 μL/24 hrs and 10 mL/kg within two weeks. Heart rate, blood pressure, and drug concentration are monitored. Systemic arterial blood pressure and heart rate are recorded by PONEMAH (Gould Instrument System, Valley View, Ohio), a pressure transducer through a data acquisition system for recording blood pressure and heart rate, for 6 to 24 hours based on experimental protocol. Mean arterial blood pressure (primary endpoint) is analyzed for assessing the efficacy of the compound.

Blood samples are analyzed for measuring plasma drug concentration, using the LC/MS/MS method described below, and for evaluating potential biomarkers.

LC/MS/MS Method

Sample Preparation: Plasma samples (50 μL unknown, control or blank) are mixed with 10 μL acetonitrile:water or a standard solution of the PDE-5 inhibiting compound and 150 μL of internal standard solution (100 ng/mL of the PDE-5 inhibiting compound in acetonitrile). The mixture is centrifuged at 3000 rpm for 5 min, and 125 μL of the supernatant transferred to a 96 well plate. The solvent is evaporated under a stream of nitrogen and the residue is reconstituted with 80 μL acetonitrile/0.1% aqueous formic acid (20:80 v/v).

A 20 μL volume of each prepared sample is injected onto a Phenomenex Synergi 4 μm MAX-RP 2.0×75 mm column and eluted at 0.4 mL/min using gradient elution from 0.1% aqueous formic acid (mobile phase A) to acetonitrile (mobile phase B). The gradient program consists of initial application of 90% mobile phase A, followed by a linear gradient to 75% mobile phase B from 0.2 to 1.15 min after injection and held at 75% mobile phase B until 2.0 min. The mobile phase was linearly changed back to 90% mobile phase A from 2.00 to 2.10 minutes, and the next injection took place at 3.00 min. Detection was performed by mass spectrometry using positive ion electrospray (ESI) with multiple reaction monitoring of the transitions m/z 454.00 (MH+ the PDE-5 inhibiting compound)→m/z 408.00, m/z 466.24 (MH+ the PDE-5 inhibiting compound)→409.33. The ion spray voltage a is set at 5000. A calibration curve is constructed by using peak area ratios of the analyte relative to the internal standard. Subject concentrations are determined by inverse prediction from their peak area ratios against the calibration curve.

Method B: Implantation of Radio Transmitters and Subsequent Blood Pressure Screening by Telemetry in Spontaneously Hypertensive Rats Spontaneously Hypertensive Rats (SHR) are anesthetized with isoflurane gas via an isoflurane anesthesia machine that is calibrated to deliver isoflurane over a range of percentages as oxygen passes through the machine's inner chambers. The animals are placed in an induction chamber and administered isoflurane at 4-5% to reach a surgical plane of anesthesia. They are then maintained at 1-2% during the surgical procedure via a nose cone, with isoflurane delivered via a smaller isoflurane anesthesia device on the surgical table.

Following administration of anesthesia, the rats are implanted with transmitters using aseptic procedures with commercially available sterile radio-telemetry units (Data Sciences, international, Roseville, Minn. 55113-1136). Prior to surgery the surgical field is shaved, scrubbed with Dial™ brand antimicrobial solution (containing 4% chlorhexidine gluconate and 4% isopropyl alcohol) followed by an application of iodine (10%) spray solution. A 2.5 to 3.0 cm laparotomy is preformed and the radio-telemetry units implanted into the abdomen, with the catheter tip inserted into the abdominal aorta. Baby Weitlaner retractors are used to retain soft tissue. A 1 cm section of the abdominal aorta is partially dissected and that section cross-clamped briefly, punctured with a 21-gauge needle and the transmitter catheter tip introduced into the vessel and secured by a single 4.0 silk suture anchored to the adjacent psoas muscle. The transmitter body is then inserted into the abdominal cavity and simultaneously secured to the abdominal muscle wall while closing with running 4.0 silk suture. The skin layer is closed with subdermal continuous 4.0 absorbable suture. A subcutaneous (s.c.) administration of marcaine followed by a topical application of iodine is administered into and around the suture line, respectively, upon closing. All rats receive a postoperative injection of buprenorphine @ 0.05 mg/kg, s.c. before regaining consciousness. A typical dose volume for a 0.300 kg rat will be 0.050 ml. The rats must be fully recovered from their operative anesthesia before the administration of buprenorphine. They then receive the same dose once daily for 2 consecutive days, unless the animal demonstrates that it is in compromising postoperative pain.

Following surgery, the rats are returned to their cages and housed individually on solid bottom caging with paper bedding. A period of no less than 7 days is allowed for recovery before experimental procedures are initiated. It has been observed that the rats are typically hypertensive for several days following surgery and return to "normotensive" levels by approximately the 7th day post-surgery. They are fed standard rat chow and water ad libitum throughout the experimental time line.

The compound is administered intragastrically (i.g.) via gavage, using of a stainless steel, 2½ inch, 18 gauge gavage needle with a balled end. For single daily dosing, the target volume is 3.33 ml/kg, i.g. The vehicles in which the compound is administered will vary depending on solubility of the compound, however, methylcellulose (0.5%) in water will be the primary choice.

Blood pressure data will be obtained using Data Sciences International's data acquisition program. Blood pressure samples are recorded at 1.5-3 minute intervals for a 5 second duration 24 hours per day for the entire study. This data is processed by Data Science's data analysis software into averages of a desired time intervals. All other data reduction is performed in Microsoft Excel™ spreadsheets.

Method C: SHR Rat

This experimental protocol is designed to screen for blood pressure lowering by N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide. The spontaneously hyperentsive rat (SHR) is cannulated in the jugular vein and carotid artery; one for compound administration and one for direct blood pressure measurement, respectively. The animals are fully conscious following surgery and all experimentation takes place within one working day. Blood pressure lowering is the primary parameter to be evaluated. However, systolic and diastolic pressure and heart rate data is collected as well. Rats will be dosed in an escalating, or cumulative manner to observe the responses following this regimen. This particular method will permit screening of multiple doses in one day using the same animals.

Methods:

Anesthesia: Rats are anesthetized with 5% isoflurane to effect. Incision sites are shaved and aseptically prepared for surgery. Rats are then transferred to the surgical field with a heating pad, supplemental isoflurane and maintained at 37° C., and isoflurane to effect throughout the surgical procedure.

Surgery: Arterial and venous cannula are implanted in the jugular vein and carotid artery, respectively. Cannulae are tunneled subcutaneously to the back of the neck where they exit percutaneously. Stainless steel staples are used to close each incision site. The cannulae are then run through a spring-tether to a swivel apparatus by which protects the cannulae from the animals chewing throughout the experiment.

Recovery: Rats are placed into an opaque polycarbonate cage instrumented with a counter balance arm that supports the weight of the tether and swivel apparatus. A paper bedding material is used to cover the bottom of the cage. The rats are allowed to recover from surgery at this point and receive 2 mL of volume early during their recovery stage. No food is provided to the animals.

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

We claim:

1. Crystalline N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide having an X-ray powder diffraction pattern comprising diffraction peaks at 3.6±0.1, 7.2±0.1, and 10.1±0.1 degrees two theta.

2. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 1 wherein the X-ray powder diffraction pattern further comprises diffraction peaks at 9.4±0.1, 18.9±0.1, and 29.1±0.1 degrees two theta.

3. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 2 wherein the X-ray powder diffraction pattern further comprises diffraction peaks at 19.4±0.1, 22.9±0.1, and 32.9±0.1 degrees two theta.

4. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 1 wherein the X-ray powder diffraction pattern further comprises diffraction peaks as depicted in FIG. 3, herein incorporated by reference.

5. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 1 further comprising a Fourier Transform infrared absorption band at 1452±2 $cm^{-1}$.

6. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 5 further comprising Fourier Transform infrared absorption bands at 722±2, 920±2, 1211±2, and 1395±2 $cm^{-1}$.

7. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 1 further comprising a Raman band at 1299±2 $cm^{-1}$.

8. The crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 7 further comprising Raman bands at 689±2, 1456±2, and 1535±2 $cm^{-1}$.

9. A pharmaceutical composition comprising a therapeutically effective amount of the crystalline N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide of claim 1, and a pharmaceutically-acceptable carrier.

10. A pharmaceutical composition comprising a therapeutically effective amount of N-[1-(2-ethoxyethyl)-5-(N-ethyl-N-methylamino)-7-(4-methylpyridin-2-yl-amino)-1H-pyrazolo[4,3d]pyrimidine-3-carbonyl]methanesulfonamide and a pharmaceutically-acceptable carrier, wherein at least about 50 weight percent of the N-[1-(2-ethoxyethyl)-5-(N-ethyl-N-methylamino)-7-(4-methylpyridin-2-yl-amino)-1H-pyrazolo[4,3-d]pyrimidine-3-carbonyl]methanesulfonamide is present as the crystalline N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide of claim 1.

* * * * *